United States Patent [19]
Hammerling et al.

[11] Patent Number: 5,883,136
[45] Date of Patent: Mar. 16, 1999

[54] ANHYDRORETINOL AND DERIVATIVES THEREOF AS ANTAGONISTS OF IMMUNE RESPONSES AND INHIBITORS OF CANCER CELL GROWTH

[75] Inventors: Ulrich Hammerling; Jochen Buck; Fadila Derguini; Koji Nakanishi, all of New York, N.Y.

[73] Assignees: Sloan-Kettering Institute for Cancer Research; The Trustees of Columbia University in the City of New York, both of New York, N.Y.

[21] Appl. No.: 478,411

[22] Filed: Jun. 7, 1995

Related U.S. Application Data

[63] Continuation-in-part of Ser. No. 420,435, Apr. 10, 1995, Pat. No. 5,610,200, and a continuation of Ser. No. 27,880, Mar. 8, 1993, abandoned.

[51] Int. Cl.$^6$ .......................... A61K 31/015; A61K 31/07
[52] U.S. Cl. .......................... 514/763; 514/725; 514/717; 514/731
[58] Field of Search .................................... 514/731, 717, 514/763, 725

[56] References Cited

PUBLICATIONS

Buck, et al., Retinol Is Essential For Growth Of Activated Human B Cells, J. Exp. Med. 171: 1613–1624 (1990).
Buck, et al., Differences in the Action and Metabolism Between Retinol and Retinoic Acid in B Lymphocytes, J. Cell Biology 115(3): 851–859 (1991).
Garbe, A., et al., Retinoids Are Important Cofactors in T Cell Activation, J. Exp. Med. 176: 109–117 (1992).
Jochen, Buck, et al., Intracellular Signaling by 14–Hydroxy–4, 14–Retro–Retinol, Science 254: 1654–1656 (1991).
Wald, George, Molecular Basis of Visual Excitation, Science 162: 230–239 (1968).
Roberts, et al., in *The Retinoids,* vol. 2 (eds. M.B. Sporn, A.B. Roberts, and D.S. Goodman) pp. 209–286 (1984).
Evans, Ronald M., The Steroid and Thyroid Hormone Receptor Superfamily, Science 240: 889–895 (1988).
Green, S. and Chambon, P., Nuclear Receptors Enhance Our Understanding of Transcription Regulation, Trends in Genet., 4: 309–314 (1988).
Leo, et al., Identification of a Monoclonal Antibody Specific for a Murine T3 Polypeptide, Proc. Natl. Acad. Sci USA 84: 1374–1378 (1987).
Gillis, et al., Long Term Culture of Tumour–Specific Cytotoxic T Cells, Nature 268: 154–156 (1977).
Cogan, et al., Binding Affinities of Retinol and Related Compounds to Retinol Binding Proteins, Eur. J. Biochem. 65: 71–78 (1976).
McClean, et al., Liquid Chromatographic Assay for Retinol (Vitamin A) and Retinol Analogs in Therapeutic Trials, Clin. Chem. 28: 693–696 (1982).
Schreckenbach, et al., Properties of the Retinal Binding Site in Bacteriorhodopsin: Use of Retinol and Retinyl Moieties as Fluorescent Probes, Photochem. Photobio. 28: 205–211 (1978).
Mallia, et al., Preparation, Properties and Metabolism of retro–3–Dehydroretinyl Acetate, Biochem. J. 109: 293–299 (1968).
Favennec, et al., The Biological Effects of Retinoids on Cell Differentiation and Proliferation, J. Clin. Chem. Clin. Biochem., 26: 479–489 (1988).
Shealy, Y., Synthesis and Evaluation of Some New Retinoids For Cancer Chemoprevention, Preventive Medicine 18: 624–645 (1989).
Muto, Y., et al., Antitumor Activity of Vitamin A and its Derivatives, Chemical Abstracts 102: 125184u (1984).

*Primary Examiner*—Keith D. MacMillan
*Attorney, Agent, or Firm*—John P. White; Cooper & Dunham LLP

[57] ABSTRACT

This invention provides methods of inhibiting the growth of cells, of treating a subject having a disease characterized by an uncontrolled growth of cells and of blocking an immune response as well as related inflammatory responses in a subject which comprises administering a compound having the structure:

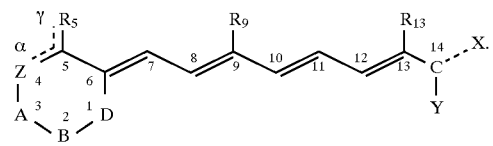

9 Claims, 17 Drawing Sheets

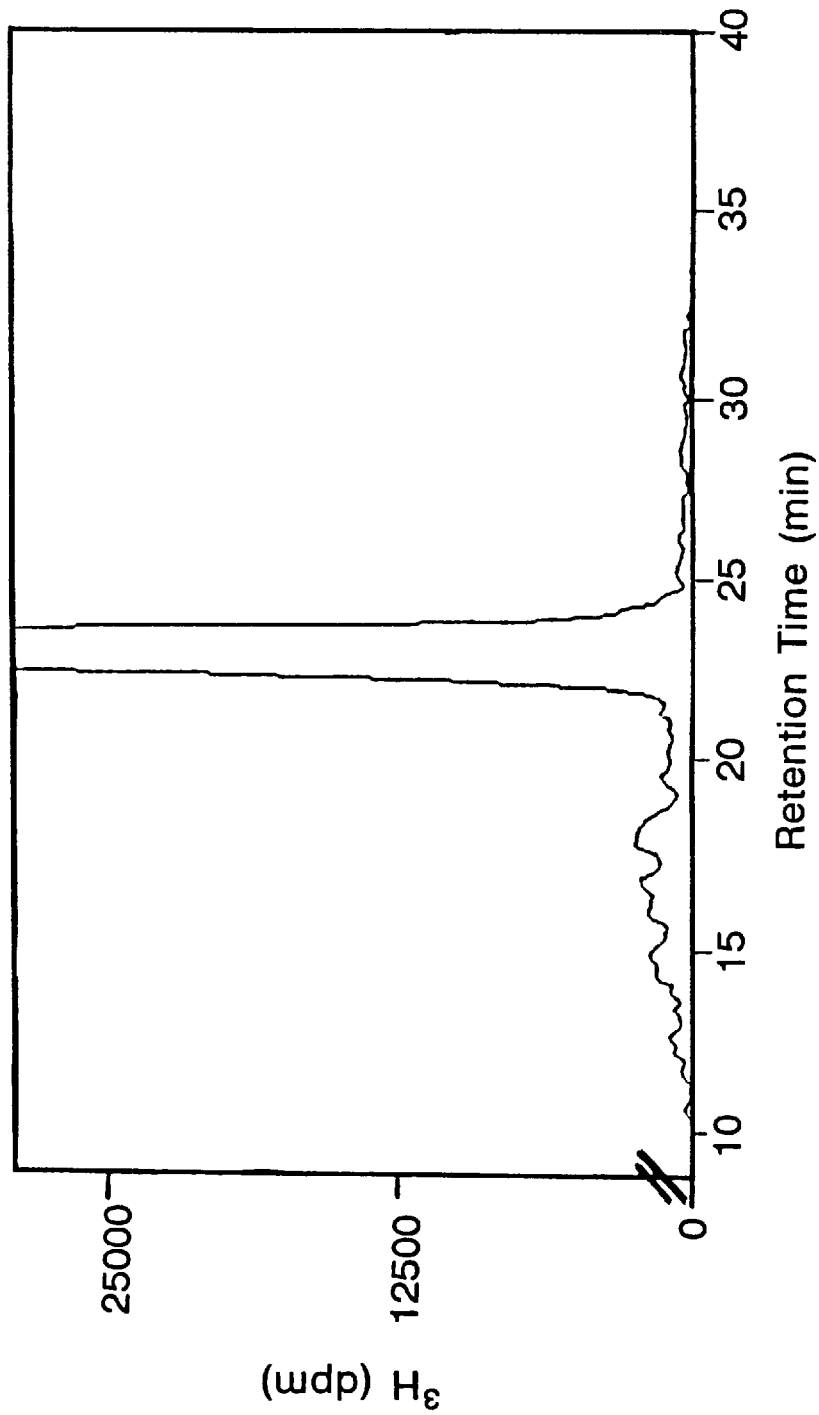

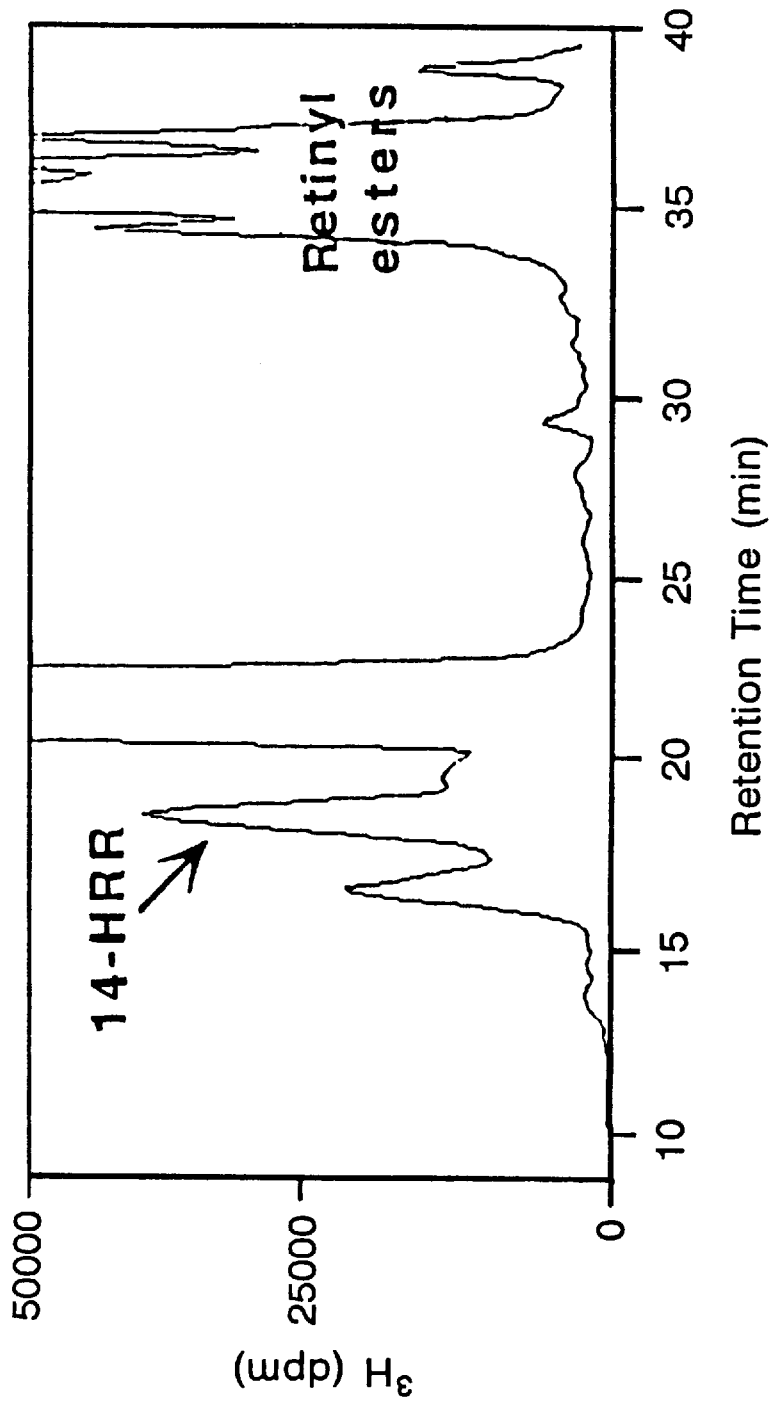

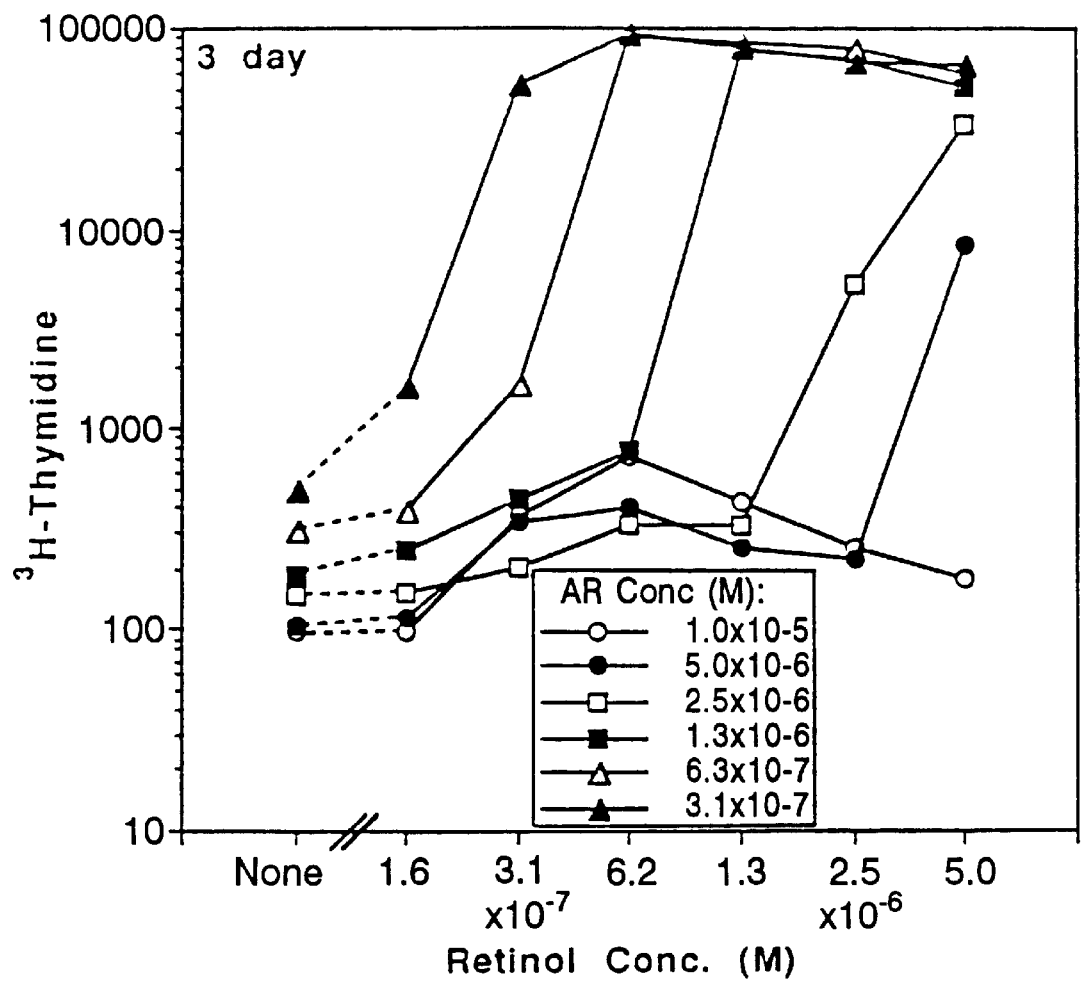

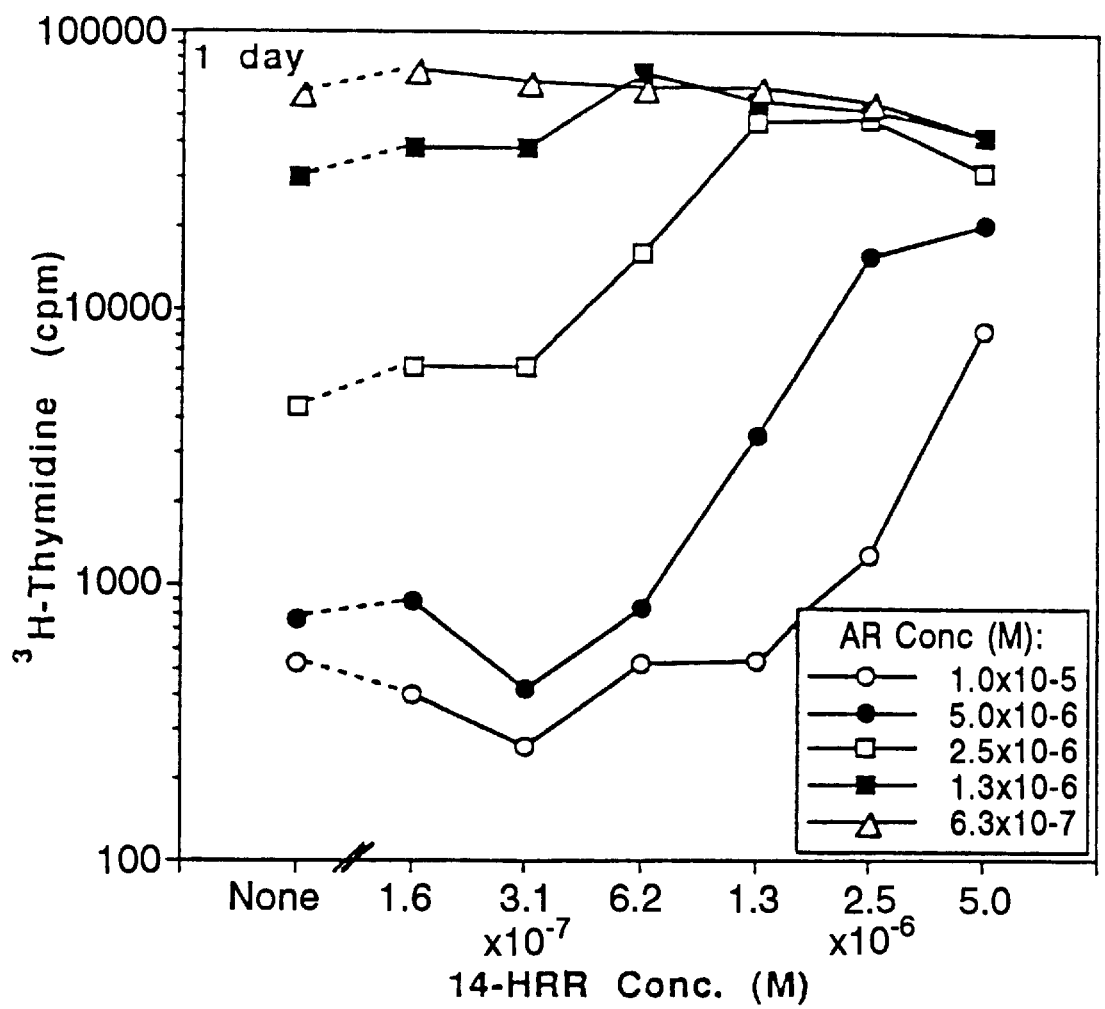

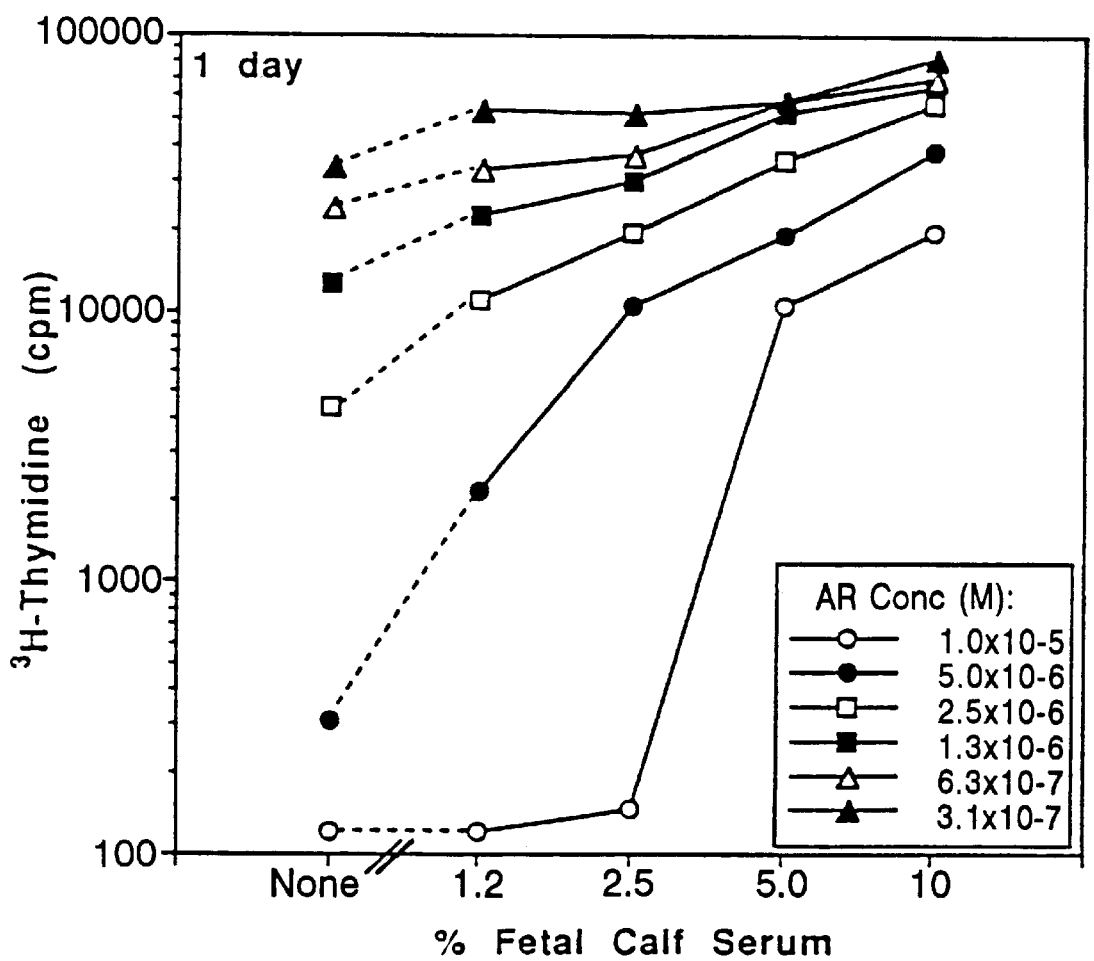

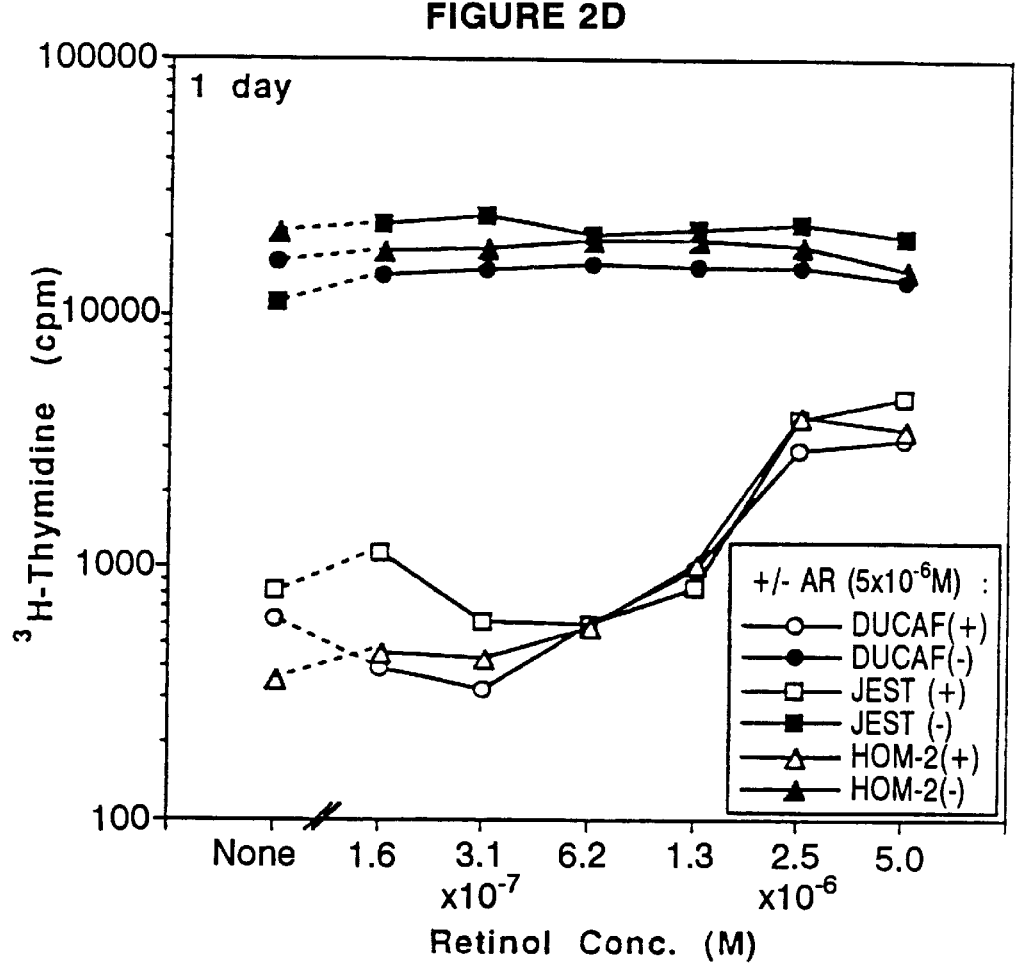

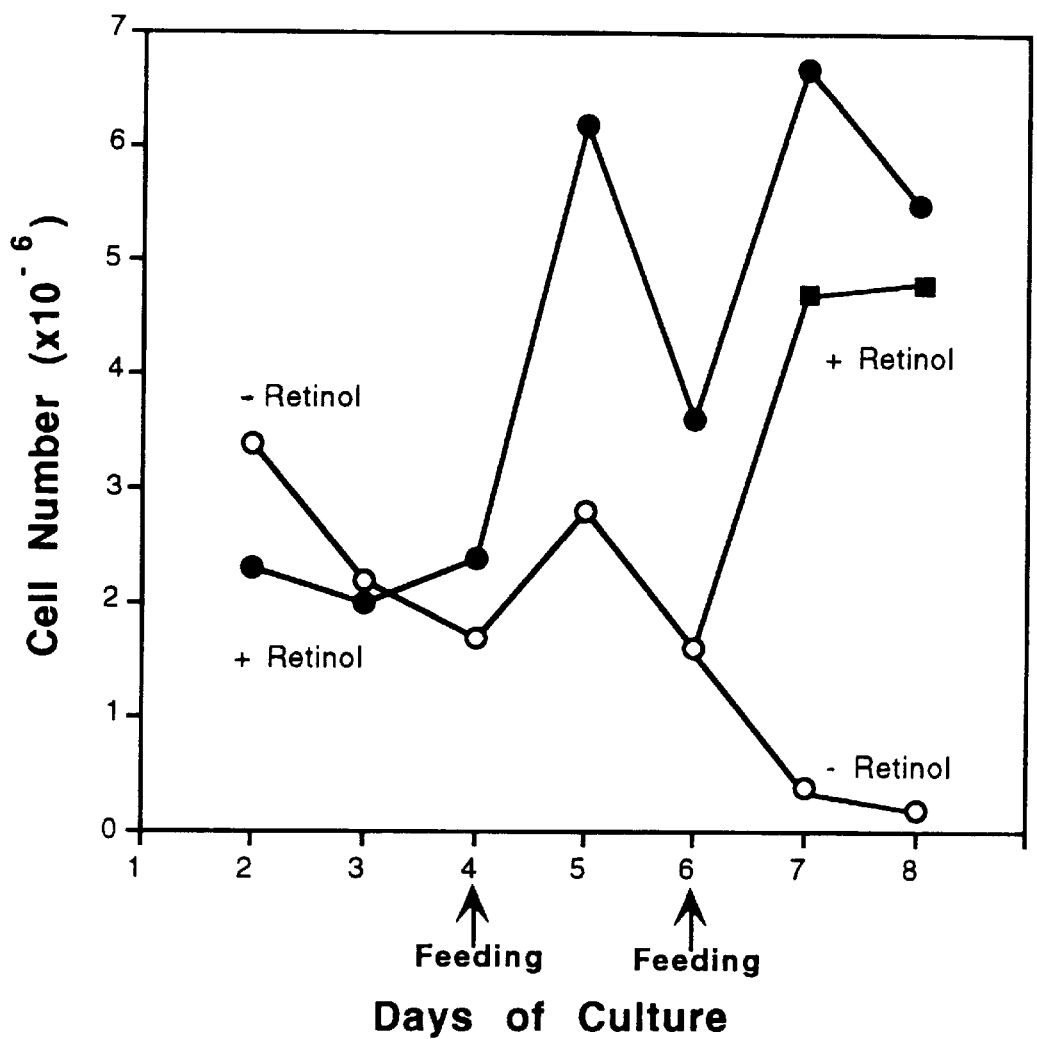

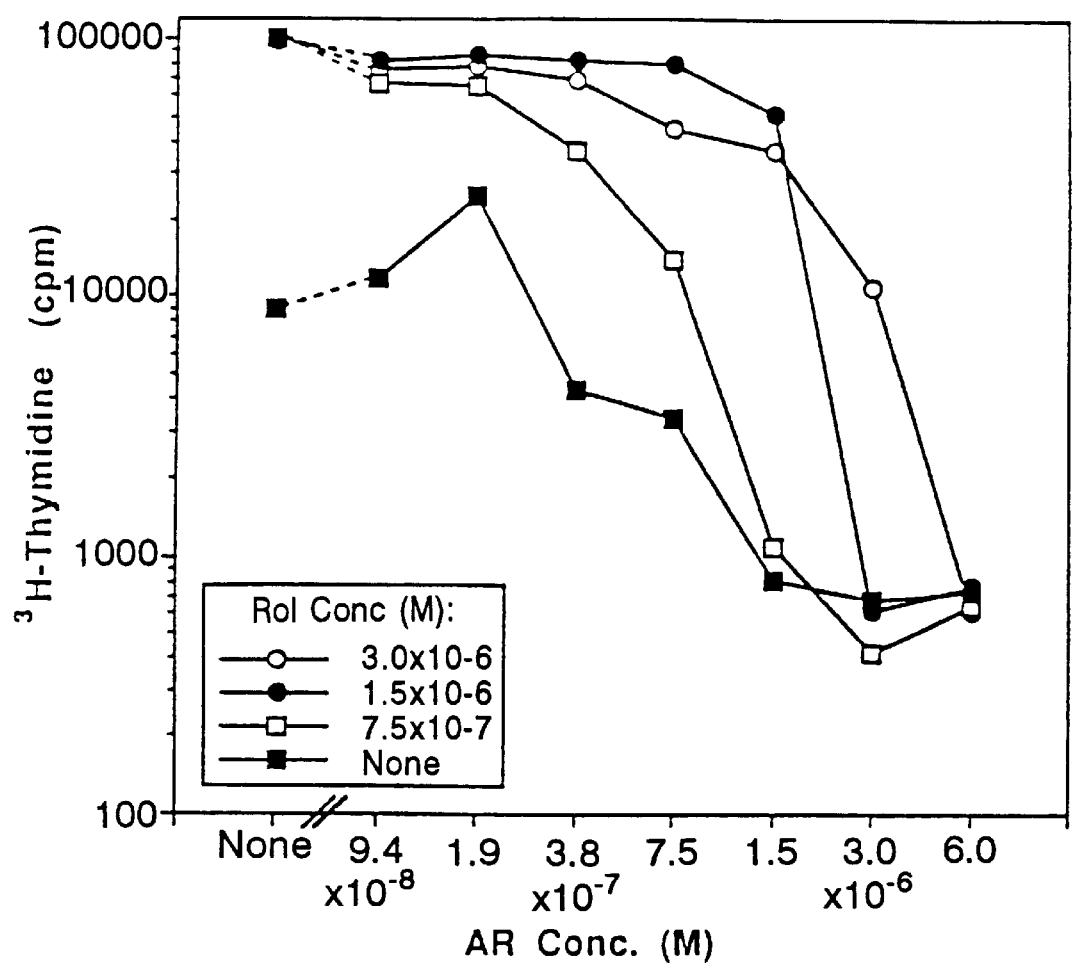

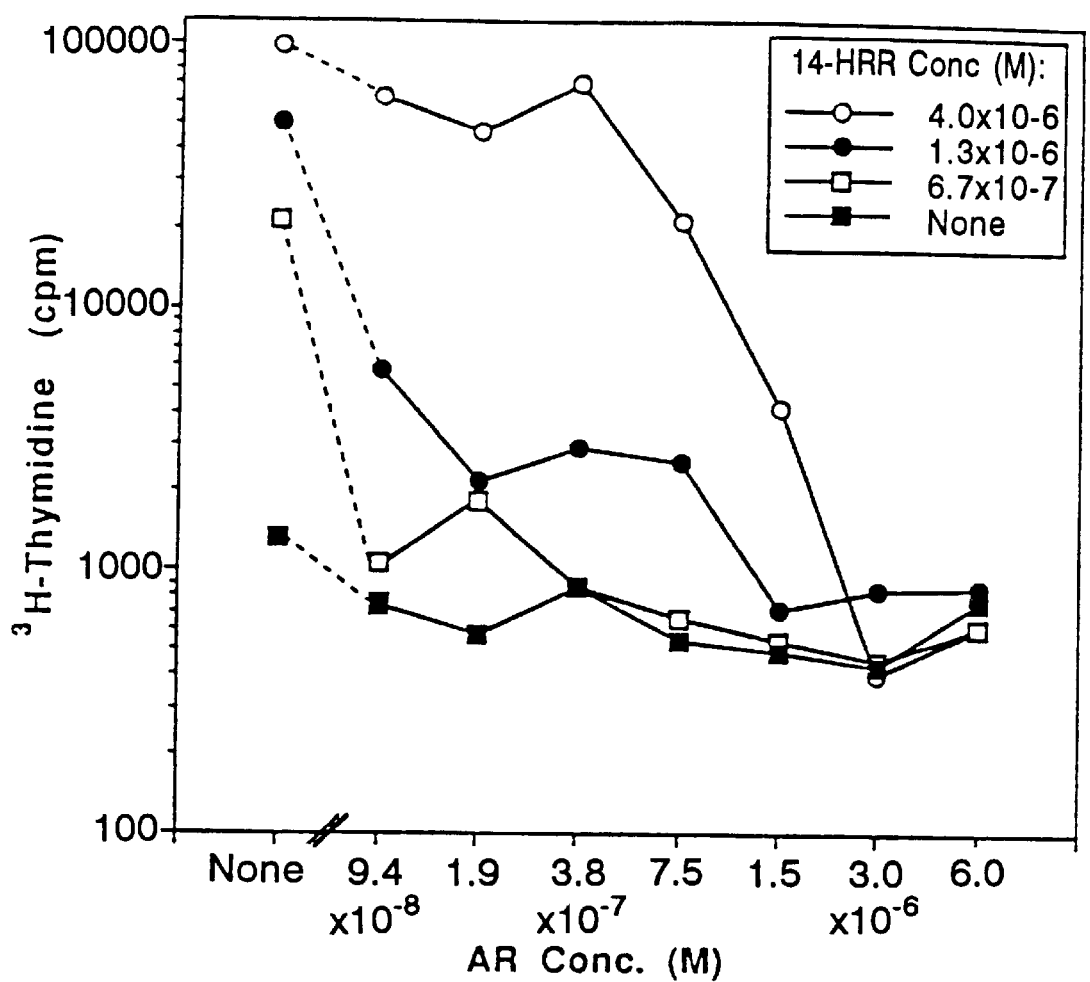

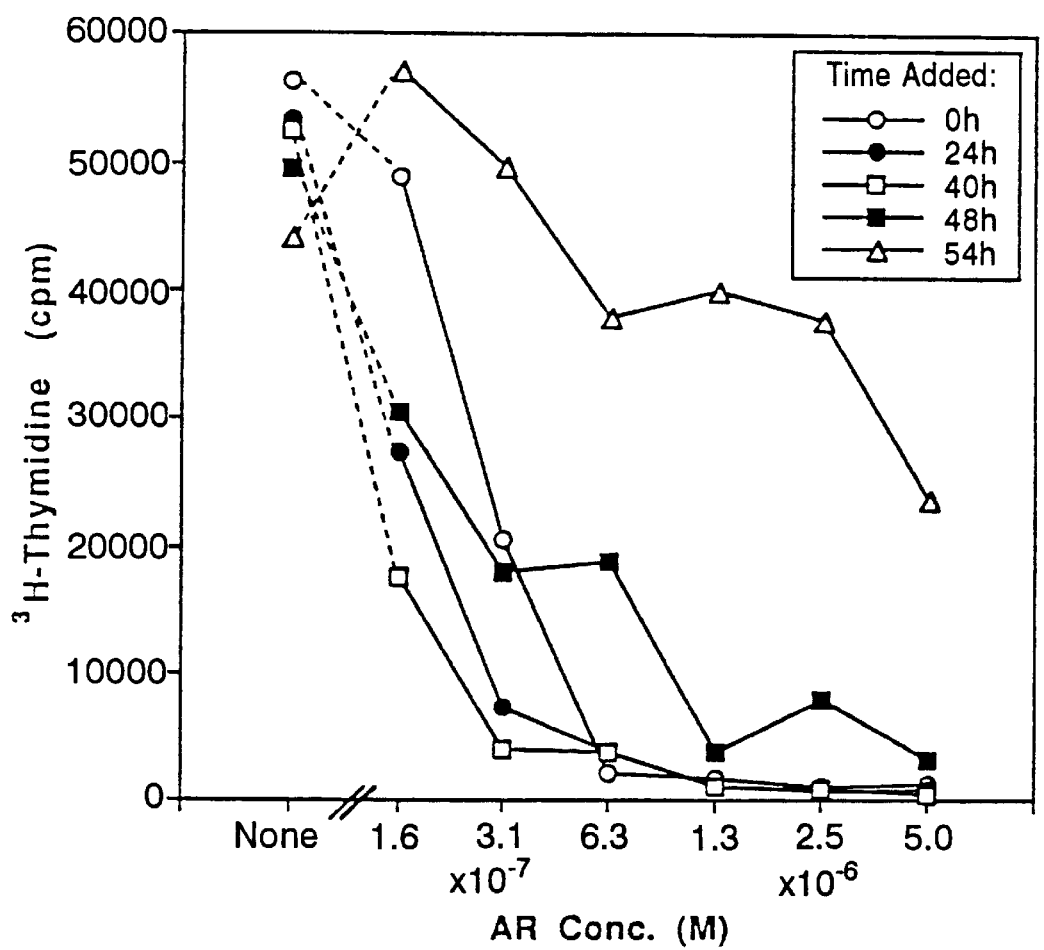

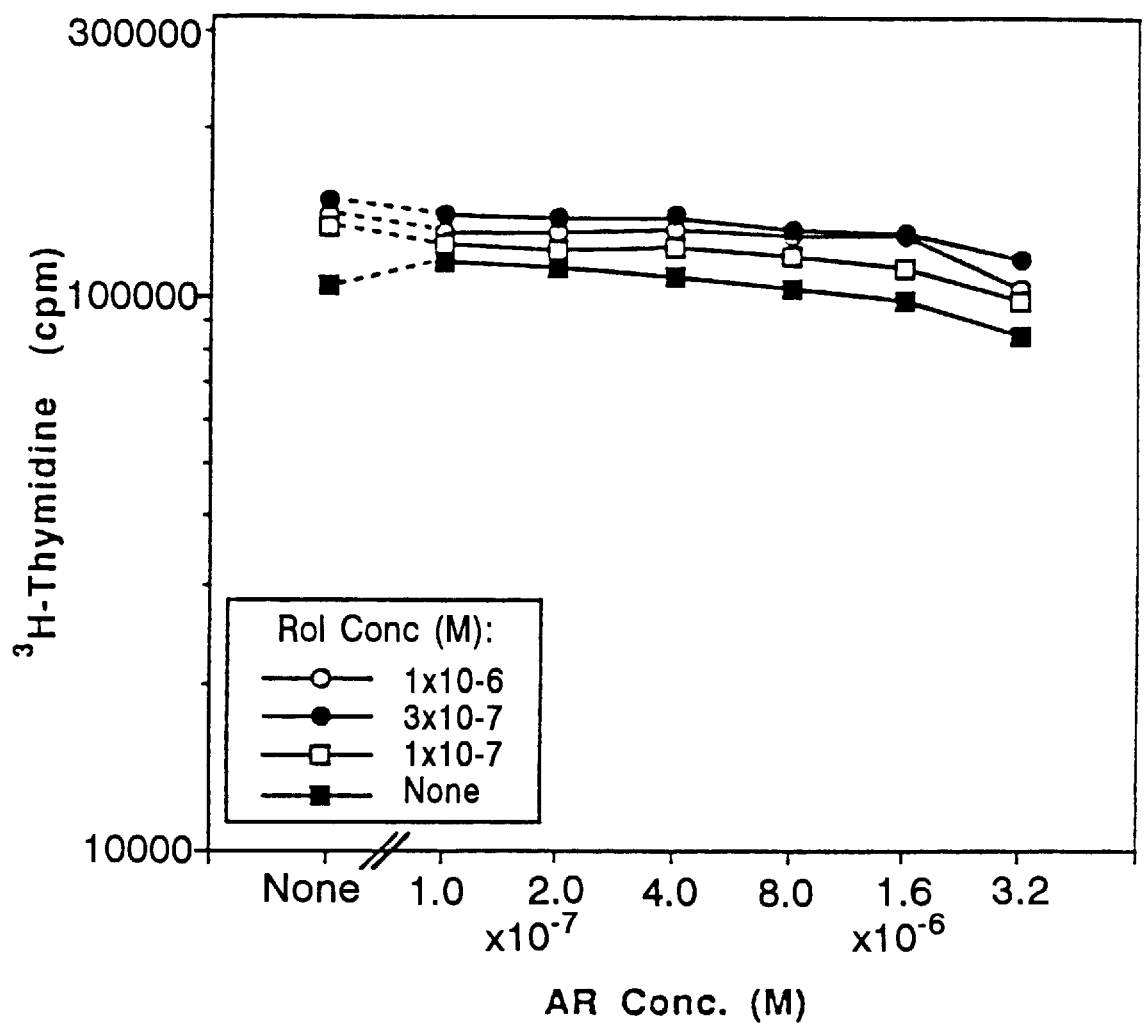

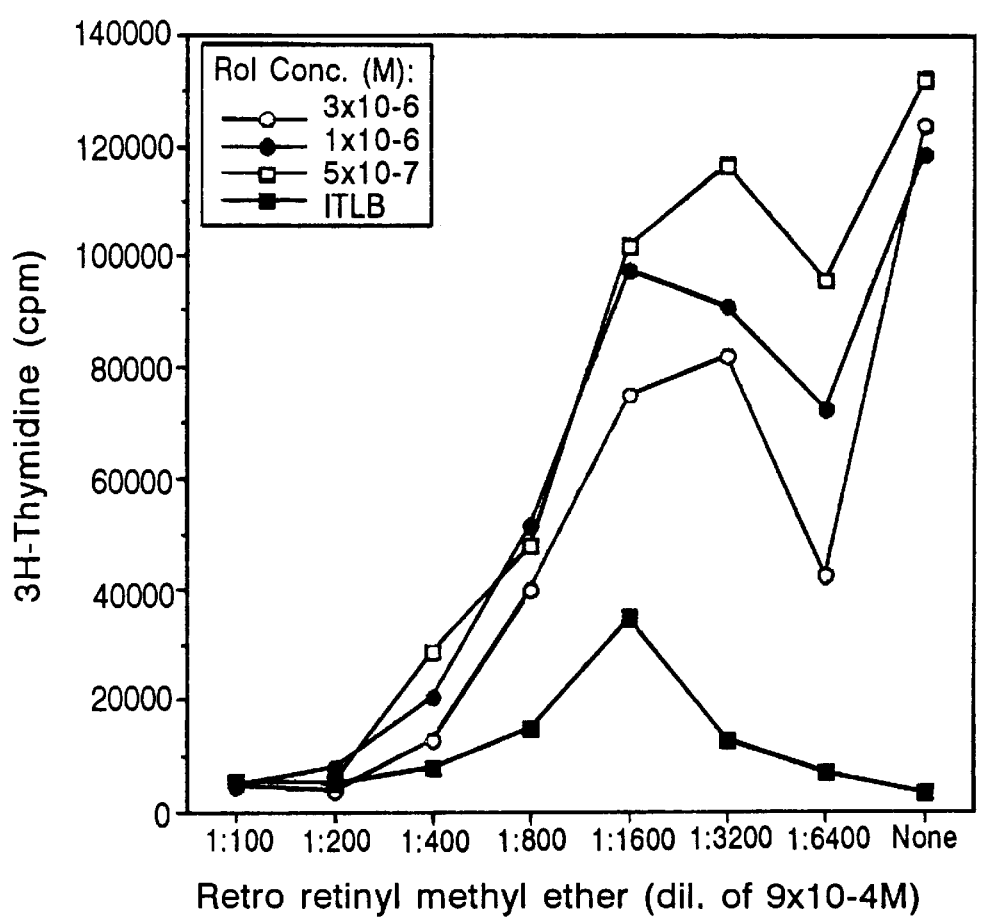

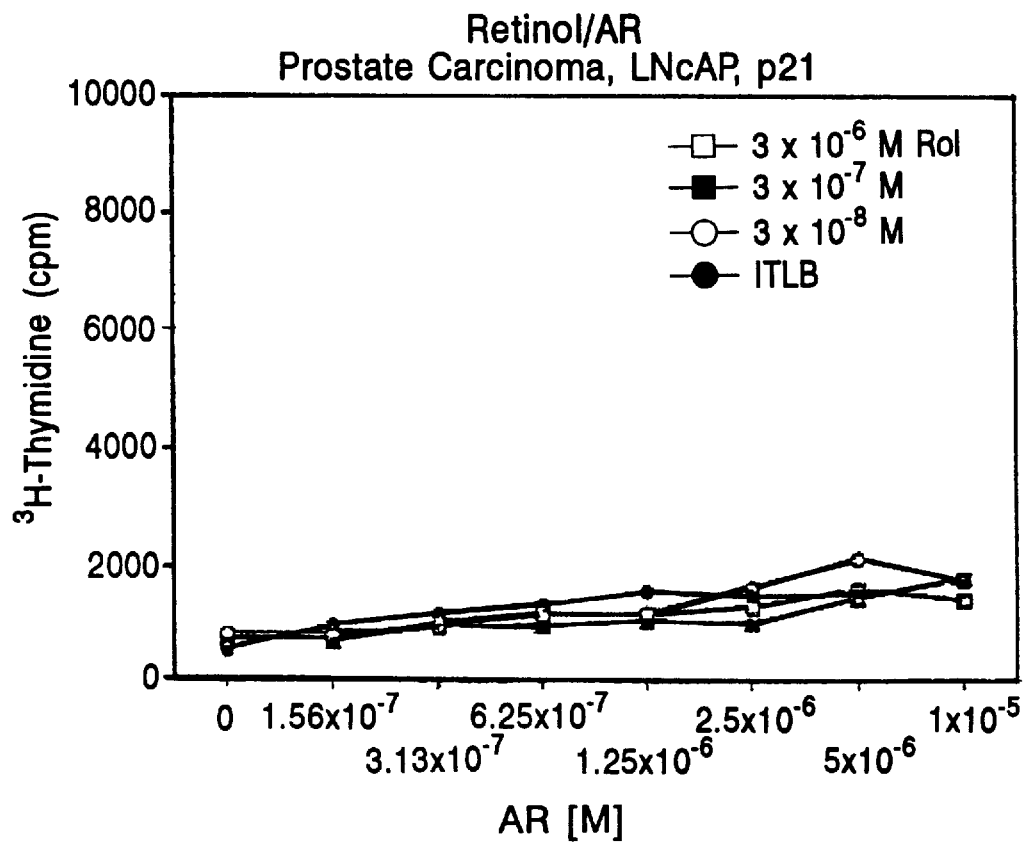

ANHYDRORETINOL AND DERIVATIVES THEREOF AS ANTAGONISTS OF IMMUNE RESPONSES AND INHIBITORS OF CANCER CELL GROWTH

This is a continuation-in-part of U.S. Ser. No. 08/420,435, filed Apr. 10, 1995, U.S. Pat. No. 5,610,200 a continuation of U.S. Ser. No. 08/027,880, filed Mar. 8, 1993, now abandoned, the contents of which are hereby incorporated by reference.

The invention described herein was made in the course of work under Grant No. CA 38351, Grant No. 49933 and Grant No. 36564 from the National Cancer Institute, National Institutes of Health, U.S. Department of Health and Human Services. The United States Government has certain rights in this invention.

BACKGROUND OF THE INVENTION

Throughout this application various publications are referenced by arabic numerals in parentheses. Full citations for these references may be found at the end of the specification immediately preceding the claims. The disclosures of these publications in their entireties are hereby incorporated by reference into this application in order to more fully describe the state of the art to which this invention pertains.

In vertebrates, many different processes as diverse as growth, vision, and reproduction are vitamin A (retinol) dependent (5). Retinol is the source for specific derivatives, i.e., retinoids, which are adapted to specified functions, such as 11-cis retinal in vision (6) or 9-cis and all-trans retinoic acid for differentiation of a number of cellular systems (7). The general mechanism of action of retinoids presumably is connected with their specific binding proteins including nuclear receptor molecules that are involved in transcriptional regulation (8,9).

Retro-retinoids are characterized by a planar ring-to-tail configuration, rigidly enforced by the rearrangement of the carbon double bond system so as to fix the hexenyl ring by a double bond to the polyene tail. The first of the natural retro-retinoids to be discovered, 14-hydroxy-4,14-retro-retinol (14-HRR), plays a role in the regulation of lymphocyte proliferation (3,4).

A general feature of retinoids in biological systems is their association with intra- and extracellular specific binding proteins. These function as carriers for transport and for protection against oxidative degradation. In specific cases, i.e., all trans-retinoic acid, nuclear receptors, involved in transcriptional regulation, are activated after binding of the retinoid ligand. Although 14-HRR-specific binding proteins and respective nuclear receptors have not yet been demonstrated, the reversible inhibition of 14-HRR by its structural analog, anhydroretinol, implies their existence.

In serum-free, defined medium, growth of transformed human B lymphocytes and antigen-receptor-mediated activation of T lymphocytes is controlled by retinol in a dose-dependent fashion, the optimum concentration range being $2 \times 10^{-7}$M to $2 \times 10^{-6}$M (1,2). Retinol is enzymatically converted in lymphocytes and other cells into 14-HRR. 14-HRR substitutes effectively for retinol when a 1 to $5 \times 10^{-8}$M concentration of exogenous 14-HRR is maintained in the medium (4).

The hydrocarbon anhydroretinol (AR), first detected in 1939 in fish liver oils (10), is structurally closely related to 14-HHR and was therefore tested for its effects on B cell proliferation.

Anhydroretinol, though a structural analog of 14-HHR, has been discovered not to aid B cell proliferation but to reversibly inhibit retinol- and 14-HHR-dependent effects and to block B lymphocyte proliferation as well as activation of resting T lymphocytes.

SUMMARY OF THE INVENTION

This invention provides a method of inhibiting the growth of cells, a method of treating a subject having a disease characterized by an uncontrolled growth of cells and a method of blocking an immune response and related inflammatory responses in a subject by use of a compound having the structure:

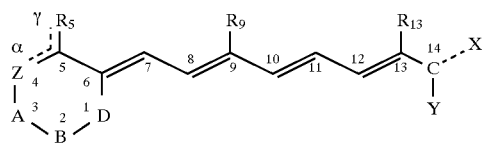

wherein Z represents:

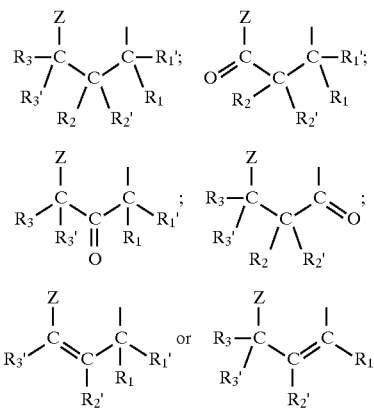

$R_1$, $R_1'$, $R_2$, $R_2'$, $R_3$ and $R_3$ are independently H, halide, $C_1$–$C_5$ alkyl or alkyl halide,

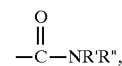

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;

$R_9$ and $R_{13}$ are H, a halide, or a $C_1$–$C_5$ alkyl or alkyl halide group;

X is —$CH_2$;

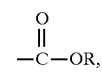

wherein R is H or $C_1$–$C_{20}$ alkyl; or $CH_2OR$, wherein R is H, a $C_1$–$C_{20}$ alkyl or has the structure:

wherein R' is H, a $C_1$–$C_{20}$ alkyl or alkyl halide, or is —NR'R" wherein each of R' and R" are independently H, or a $C_1$–$C_{20}$ alkyl group;

the dashed line between $C_{14}$ and X represents a single bond when

X is —$CH_2OR$ or

and a double bond when X is —$CH_2$;

Y is H;

the double bonds between $C_6$ and $C_7$, $C_8$ and $C_9$, $C_{10}$ and $C_{11}$, and $C_{12}$ and $C_{13}$ can have Z or E configuration; the absolute configuration at $C_{14}$ is either R or S; and the dashed line at $C_5$ represents a double bond which can be either α or γ, wherein when the double bond at $C_5$ is γ $R_5$ is $C_1$–$C_5$ alkylidene or haloalkylidene and Z is C=O or $CR_4R_4'$ wherein $R_4$ and $R_4'$ are independently the same as $R_1$ and $R_1'$ through $R_3$ and $R_3'$ defined above; wherein when the double bond at $C_5$ is α $R_5$ is $C_1$–$C_5$ alkyl or alkylhalide and Z is $CR_4'$ wherein $R_4'$ is the same as defined above.

BRIEF DESCRIPTION OF FIGURES

FIGS. 1A–1D High pressure liquid chromatography and U.V. spectra of retinoids.

FIG. 1A: Source of retinoids: insect SF-9

FIG. 1B: Source of retinoids: insect SF 21

FIG. 1C: Source of retinoids: Human lymphoblastoid 5/2 cells

FIG. 1D: U.V. spectrum of all-trans anhydroretinol

FIGS. 2A–2D Anhydroretinol as an antagonist and reversible inhibitor of B lymphocyte proliferation.

FIG. 2A: all-trans retinol

FIG. 2B: 14-HRR

FIG. 2C: Fetal calf serum. Serum contains 1–2×$10^6$M all-trans retinol.

FIG. 2D: Three additional human lymphoblastoid cell lines, Hom 2, Jest and Ducaf were tested under the conditions specified for FIG. 2A.

FIG. 3 Inhibition of human T cell leukemia cells.

FIG. 3: Cells of the human T cell line Jurkat were cultured in serum-free medium with 2×$10^{-6}$M (●) or without (○) retinol. Viable cells in each culture were counted. On days 4 and 6 nutrients were replenished. On day 6 the Rol-minus culture was split and one culture continued without retinol (○) whereas the other received 2×$10^{-6}$M retinol (■).

FIGS. 4A–4D Anhydroretinol as antagonist of induction of thymocyte proliferation, but not interleukin-2 production.

FIG. 4A: Retinol

FIG. 4B: 14-Hydroxy-retro-retinol

FIG. 4C: The time of addition of AR at different concentrations was varied from 0 hours to 54 hours after initiation of cultures with Anti-CD3ε plus 2×$10^{-6}$M retinol. The results of cell proliferation assays performed at 72 hours are shown.

FIG. 4D: CTLL Cell line proliferation measured by $^3H$ thymidine incorporation into DNA.

FIG. 5 Effective concentration range of retro-retinyl-methyl-ether in reversing the growth-promoting effect of retinol.

FIGS. 6A–6C Inhibition of proliferation of prostate cell lines DU145 (FIG. 6A), PC-3 (FIG. 6B) and LNcAP (FIG. 6C) by anhydroretinol.

DETAILED DESCRIPTION OF THE INVENTION

Figure 1B:
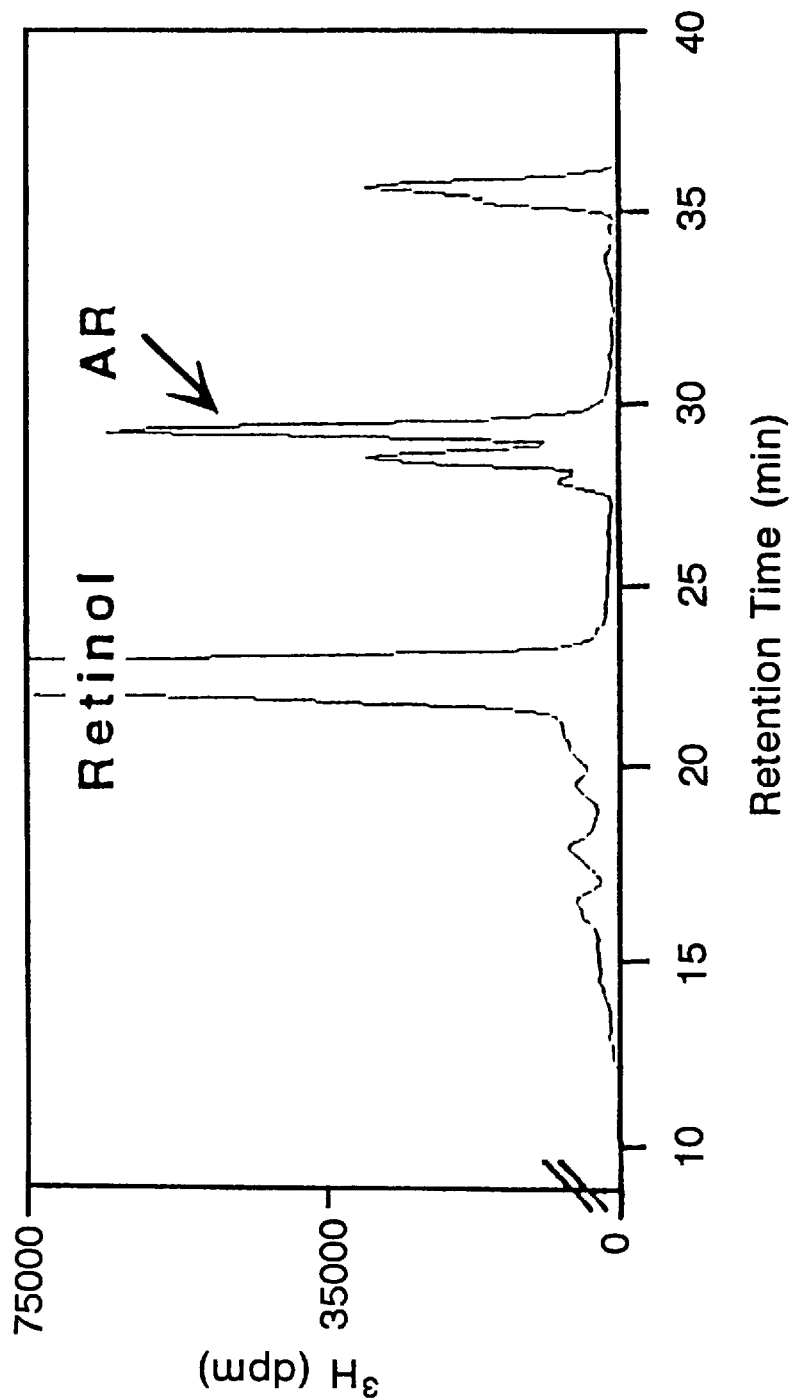

This invention provides a method of inhibiting the growth of cells which comprises contacting the cells with an effective cell growth controlling amount of a compound having the structure:

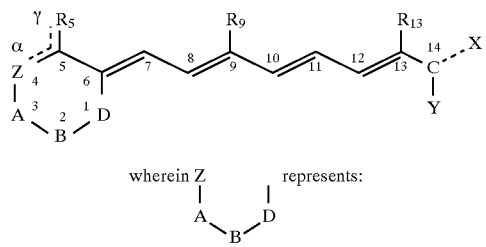

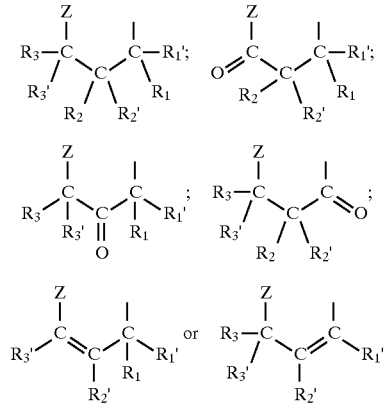

$R_1$, $R_1'$, $R_2$, $R_2'$, $R_3$ and $R_3'$ are independently H, halide, $C_1$–$C_5$ alkyl or alkyl halide,

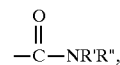

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;

$R_9$ and $R_{13}$ are H, a halide, or a $C_1$–$C_5$ alkyl or alkyl halide group;

X is —CH$_2$;

wherein R is H or C$_1$–C$_{20}$ alkyl; or CH$_2$OR, wherein R is H, a C$_1$–C$_{20}$ alkyl or has the structure:

wherein R' is H, a C$_1$–C$_{20}$ alkyl or alkyl halide, or is —NR'R" wherein each of R' and R" are independently H, or a C$_1$–C$_{20}$ alkyl group;
the dashed line between C$_{14}$ and X represents a single bond when
X is —CH$_2$OR or

and a double bond when X is —CH$_2$;
Y is H;
the double bonds between C$_6$ and C$_7$, C$_8$ and C$_9$, C$_{10}$ and C$_{11}$, and C$_{12}$ and C$_{13}$ can have Z or E configuration; the absolute configuration at C$_{14}$ is either R or S; and the dashed line at C$_5$ represents a double bond which can be either α or γ,
wherein when the double bond at C$_5$ is γ R$_5$ is C$_1$–C$_5$ alkylidene or haloalkylidene and z is C=O or CR$_4$R$_4$' wherein R$_4$ and R$_4$' are independently the same as R$_1$ and R$_1$' through R$_3$ and R$_3$' defined above; wherein when the double bond at C$_5$ is α R$_5$ is C$_1$–C$_5$ alkyl or alkylhalide and Z is CR$_4$' wherein R$_4$' is the same as defined above;
and thereby inhibit the growth of the cells.

For the purposes of this invention, the effective amount is any amount effective to inhibit the growth of the cells. The effective amount may be an amount wherein the concentration range of anhydroretinol is 1×10$^{-5}$M to 3×10$^{-7}$M. "Contacting" in the practice of this method can be in vivo or in vitro. Methods of contacting compounds to cells in vitro are well known to those of ordinary skill in the art. Several methods are demonstrated herein in the Experimental Details Section which follows. Methods of contacting the compounds to cells in vivo include all methods of administering a compound to an animal, for example as part of a pharmaceutical composition. Modes of administration of the compounds, either alone or incorporated in a pharmaceutical composition, in the methods disclosed herein are further discussed below and are useful for in vivo contacting of the compounds.

In one embodiment of this invention the cells are growth-dependent on retinol. In another embodiment of this invention, the cells are growth-dependent on 14-hydroxy-4,14-retro-retinol. Examples of cells which are growth-dependent on retinol or 14-hydroxy-4,14-retroretinol are well known to those skilled in the art. Examples include, but are not limited to, tumor cells, activated T cells, transformed B cells and myeloid cells. Examples of tumor cells include, but are not limited to, T-cell lymphomas, T-cell leukemias, B-cell lymphomas, B-cell leukemias, myeloid leukemia cells and cancer cells such as breast cancer cells.

In one embodiment of this invention the compound has the structure:

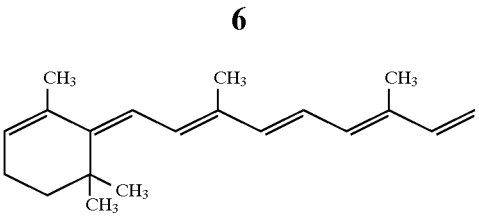

In another embodiment of this invention the compound has the structure:

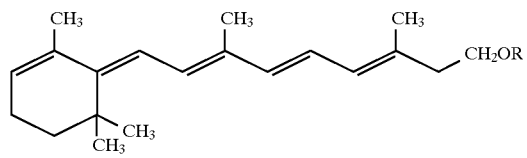

wherein R is H or a C$_1$–C$_{20}$ alkyl group.

In a further embodiment of this invention the compound has the structure:

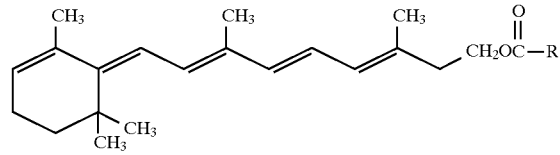

wherein R is H or a C$_1$–C$_{20}$ alkyl group.

In a further embodiment of this invention, the compound has the structure:

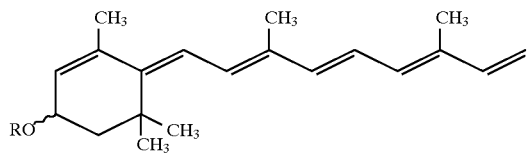

wherein R is H or a C$_1$–C$_5$ alkyl group.

This invention also provides a method of treating a subject having a disease characterized by an uncontrolled growth of cells comprising administering to the subject a pharmaceutical composition which comprises a pharmaceutically acceptable carrier and an effective cell growth controlling amount of a compound having the structure:

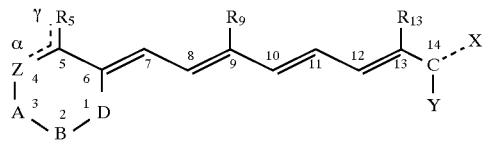

wherein Z  represents:

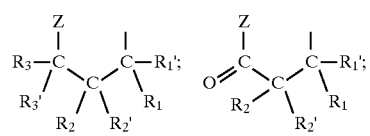

-continued

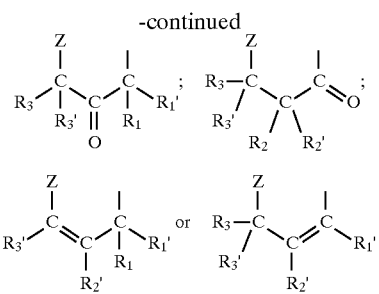

$R_1$, $R_1'$, $R_2$, $R_2'$, $R_3$ and $R_3$ are independently H, halide, $C_1$–$C_5$ alkyl or alkyl halide,

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;
$R_9$ and $R_{13}$ are H, a halide, or a $C_1$–$C_5$ alkyl or alkyl halide group;
X is —$CH_2$;

wherein R is H or $C_1$–$C_{20}$ alkyl; or $CH_2OR$, wherein R is H, a $C_1$–$C_{20}$ alkyl or has the structure:

wherein R' is H, a $C_1$–$C_{20}$ alkyl or alkyl halide, or is —NR'R" wherein each of R' and R" are independently H, or a $C_1$–$C_{20}$ alkyl group;
the dashed line between $C_{14}$ and X represents a single bond when
X is —$CH_2OR$ or

and a double bond when X is —$CH_2$;
Y is H;
the double bonds between $C_6$ and $C_7$, $C_8$ and $C_9$, $C_{10}$ and $C_{11}$, and $C_{12}$ and $C_{13}$ can have Z or E configuration; the absolute configuration at $C_{14}$ is either R or S; and the dashed line at $C_5$ represents a double bond which can be either α or γ,
wherein when the double bond at $C_5$ is γ $R_5$ is $C_1$–$C_5$ alkylidene or haloalkylidene and Z is C=O or $CR_4R_4'$ wherein $R_4$ and $R_4'$ are independently the same as $R_1$ and $R_1'$ through $R_3$ and $R_3'$ defined above; wherein when the double bond at $C_5$ is α $R_5$ is $C_1$–$C_5$ alkyl or alkylhalide and Z is $CR_4'$ wherein $R_4'$ is the same as defined above;

so as to thereby inhibit the growth of the cells.

For the purposes of this invention, the term "effective cell growth controlling amount" means any amount of the compound administered to a subject which is effective to inhibit the growth of the cells within the subject.

In the practice of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered.

In one embodiment of this invention the cells are growth-dependent on retinol. In another embodiment of this invention, the cells are growth-dependent on 14 hydroxy-4, 14-retro-retinol. Examples of cells which are growth-dependent on retinol or 14 hydroxy-4,14-retro-retinol are well known to those skilled in the art. Examples include, but are not limited to, tumor cells, activated T cells, transformed B cells and myeloid cells. Examples of tumor cells include, but are not limited to, T-cell lymphomas, T-cell leukemias, B-cell lymphomas, B-cell leukemias, myeloid leukemia cells and cancer cells such as breast cancer cells.

In one embodiment of this invention the compound has the structure:

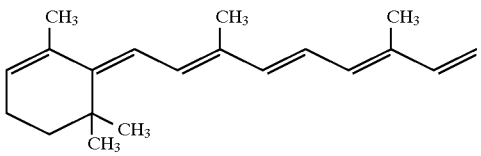

In another embodiment of this invention the compound has the structure:

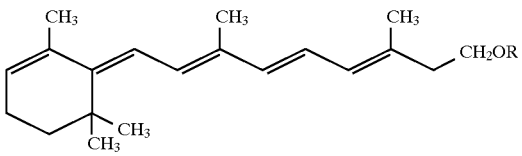

wherein R is H or a $C_1$–$C_{20}$ alkyl group.

In a further embodiment of this invention the compound has the structure:

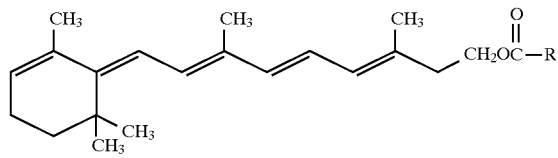

wherein R is H or a $C_1$–$C_{20}$ alkyl group.

In a further embodiment of this invention, the compound has the structure:

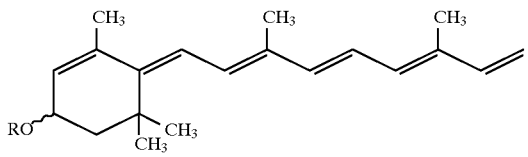

wherein R is H or a $C_1$–$C_5$ alkyl group.

In the preferred embodiment, the compound is administered in a pharmaceutical composition which comprises the compound and a pharmaceutically acceptable carrier. As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperetoneal administration of the compounds is the triglyceride emulsion commercially known as Intralipid®.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the preferred embodiment of the invention, the pharmaceutically acceptable carrier also comprises specific binding proteins, which may be, but are not limited to retinol binding protein (RBP), transthyretin (TTR), the complex formed by RBP and TTR, or albumin. Compositions comprising such carriers are formulated by well known conventional methods. However, the composition comprising anhydroretinol and a pharmaceutically acceptable carrier in an amount effective to inhibit the growth of cells which are growth dependent on retinol or 14-hydroxy-retro-retinol is previously unknown.

In the practice of this invention, the administration of the pharmaceutical composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments or transdermal patches.

This invention further provides a method of blocking an immune response in a subject which comprises administering to the subject a pharmacuetical compostion which comprises a pharmaceutically acceptable carrier and an effective immune response blocking amount of a compound having the structure:

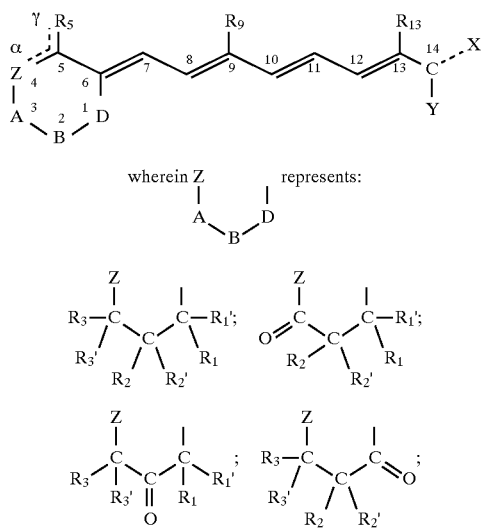

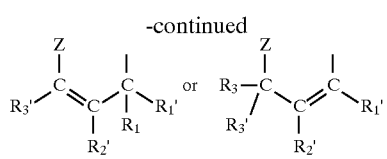

$R_1$, $R_1'$, $R_2$, $R_2'$, $R_3$ and $R_3$ are independently H, halide, $C_1$–$C_5$ alkyl or alkyl halide,

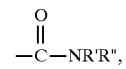

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;
$R_9$ and $R_{13}$ are H, a halide, or a $C_1$–$C_5$ alkyl or alkyl halide group;
X is —$CH_2$;

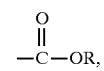

wherein R is H or $C_1$–$C_{20}$ alkyl; or $CH_2OR$, wherein R is H, a $C_1$–$C_{20}$ alkyl or has the structure:

wherein R' is H, a $C_1$–$C_{20}$ alkyl or alkyl halide, or is —NR'R" wherein each of R' and R" are independently H, or a $C_1$–$C_{20}$ alkyl group;
the dashed line between $C_{14}$ and X represents a single bond when
X is —$CH_2OR$ or

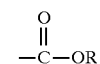

and a double bond when X is —$CH_2$;
Y is H;
the double bonds between $C_6$ and $C_7$, $C_8$ and $C_9$, $C_{10}$ and $C_{11}$, and $C_{12}$ and $C_{13}$ can have Z or E configuration; the absolute configuration at $C_{14}$ is either R or S; and the dashed line at $C_5$ represents a double bond which can be either α or γ,
wherein when the double bond at $C_5$ is γ $R_5$ is $C_1$–$C_5$ alkylidene or haloalkylidene and Z is C=O or $CR_4R_4'$ wherein $R_4$ and $R_4'$ are independently the same as $R_1$ and $R_1'$ through $R_3$ and $R_3'$ defined above; wherein when the double bond at $C_5$ is α $R_5$ is $C_1$–$C_5$ alkyl or alkylhalide and Z is $CR_4'$ wherein $R_4'$ is the same as defined above;
effective to block the immune response.

For the purposes of this invention the term "effective immune response blocking amount" means any amount of the compound administered to a subject which is effective to inhibit an immune response within the subject.

In the practice of the method of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed, and the frequency with which the composition is to be administered.

In the practice of the invention, the above-identified compound is effective to supress either the subject's cellular immune response or humoral immune response.

The cellular immune response to which the compound is effective is the subject's cellular immune response which is mediated by the subject's $CD4^+$ T cells or by $CD8^+$ T cells.

The specific target of the humoral immune response to which the invention is effective is the subject's antibody-forming B lymphocytes. Diseases which are characterized by such a humoral immune response in a subject are well known to those skilled in the art. Examples of such diseases include, but are not limited to, graft versus host disease, psoriasis, allergic reactions and autoimmune diseases. The compounds of the invention are also effective against immune responses due to transplantation into the subject, including but not limited to such organs as kidney, heart or lung, and bone marrow transplantation.

Examples of allergic reactions in a subject are well known to those skilled in the art and include allergic reactions due to external as well as internal stimuli. For the purposes of this invention, "external stimuli" are stimulants which cause an allergic reaction in a subject as a result of their contact the outer suface of the subject. Examples of allergic reactions which result from "external stimuli" include, but are not limited to, chemical dermatitis or contact allergies resulting from contact of the subject with such stimuli as poison ivy, poison oak, poison sumac or insect venom.

For the purposes of this invention, "internal stimuli" are stimulants which cause an allergic reaction in a subject as a result of their being inhaled, injested or transmitted below the outer surface of the subject. Examples of allergic reactions which result from "internal stimuli" include, but are not limited to, administration of other medicomments, allergies reactions to or beverages food and allergic reactions resulting from the internalization in a subject of airborne allergens such as smoke or pollin.

Examples of autoimmune diseases against which this invention would be effective include, but are not limited to, rheumatoid arthritis, nephrosis, thyroiditis and diabetes mellitus.

In one embodiment of this invention the compound has the structure:

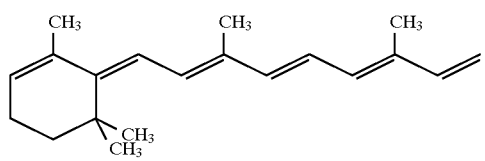

In another embodiment of this invention the compound has the structure:

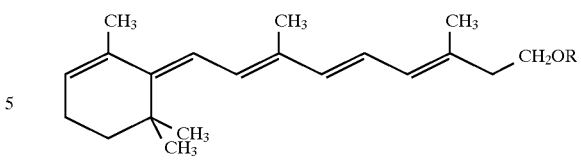

wherein R is H or a $C_1$–$C_{20}$ alkyl group.

In a further embodiment of this invention the compound has the structure:

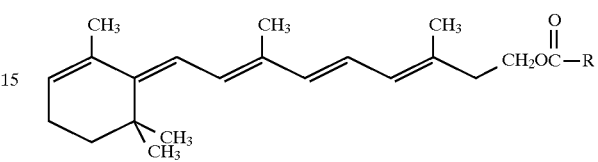

wherein R is H or a $C_1$–$C_{20}$ alkyl group.

In a further embodiment of this invention, the compound has the structure:

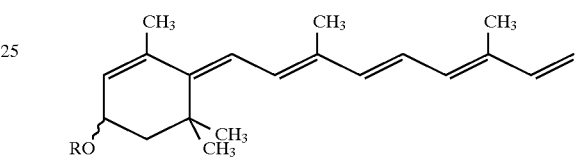

wherein R is H or a $C_1$–$C_5$ alkyl group.

In the preferred embodiment, the compound is administered in a pharmaceutical composition which comprises the compound and a pharmaceutically acceptable carrier. As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptible triglyceride emulsion useful in intravenous and intraperetoneal administration of the compounds is the triglyceride emulsion commercially known as Intralipid®.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the preferred embodiment of the invention, the pharmaceutically acceptable carrier also comprises specific binding proteins, which may be, but are not limited to retinol binding protein (RBP), transthyretin (TTR), the complex formed by RBP and TTR, or albumin. Compositions comprising such carriers are formulated by well known conventional methods. However, the composition comprising anhydroretinol or a pharmaceutically acceptable salt thereof in an amount effective to supress an immune response is previously unknown.

In the practice this invention, the administration of the pharmacuetical composition may be effected by any of the well known methods including, but not limited to, oral, intravenous, interperitoneal, intramuscular, subcutaneous or topical administration. Topical administration can be effected by any method commonly known to those skilled in the art including, but are not limited to, incorporation of the pharmaceutical composition into creams, ointments or transdermal patches.

Lastly, the invention provides a method of blocking an inflammatory response in a subject which comprises administering to the subject a pharmaceutical composition which comprises a pharmaceutically acceptable carrier and an effective inflamatory response blocking amount of a compound having the structure:

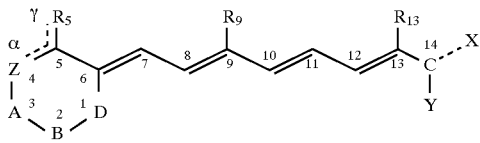

wherein Z represents:

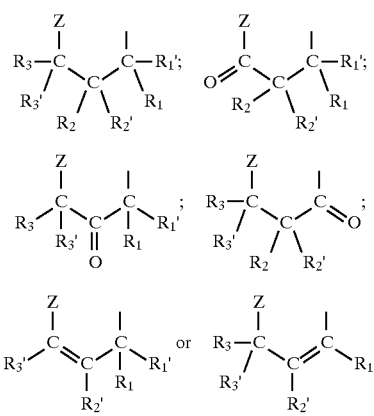

$R_1$, $R_1'$, $R_2$, $R_2'$, $R_3$ and $R_3$ are independently H, halide, $C_1$–$C_5$ alkyl or alkyl halide,

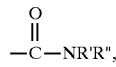

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;
$R_9$ and $R_{13}$ are H, a halide, or a $C_1$–$C_5$ alkyl or alkyl halide group;
X is —$CH_2$;

wherein R is H or $C_1$–$C_{20}$ alkyl; or $CH_2OR$, wherein R is H, a $C_1$–$C_{20}$ alkyl or has the structure:

wherein R' is H, a $C_1$–$C_{20}$ alkyl or alkyl halide, or is —NR'R" wherein each of R' and R" are independently H, or a $C_1$–$C_{20}$ alkyl group;
the dashed line between $C_{14}$ and X represents a single bond when X is —$CH_2OR$ or

and a double bond when X is —$CH_2$;

Y is H;

the double bonds between $C_6$ and $C_7$, $C_8$ and $C_9$, $C_{10}$ and $C_{11}$, and $C_{12}$ and $C_{13}$ can have Z or E configuration; the absolute configuration at $C_{14}$ is either R or S; and the dashed line at $C_5$ represents a double bond which can be either α or γ, wherein when the double bond at $C_5$ is γ $R_5$ is $C_1$–$C_5$ alkylidene or haloalkylidene and Z is C=O or $CR_4R_4'$ wherein $R_4$ and $R_4'$ are independently the same as $R_1$ and $R_1'$ through $R_3$ and $R_3'$ defined above; wherein when the double bond at $C_5$ is α $R_5$ is $C_1$–$C_5$ alkyl or alkylhalide and Z is $CR_4'$ wherein $R_4'$ is the same as defined above;

to thereby block the imflammatory response.

For the purposes of this invention, the term "effective inflammatory response blocking amount" means any amount of the compound administered to a subject which is effective to inhibit an inflammatory response within the subject.

In the practice of this invention the amount of the compound incorporated in the composition may vary widely. Factors considered when determining the precise amount are well known to those skilled in the art. Examples of such factors include, but are not limited to, the subject being treated, the specific pharmaceutical carrier and route of administration being employed, and the frequency with which the composition is to be administered.

The inflammatory responses against which the compound of this invention is effective are inflammatory responses mediated by the subject's T lymphocytes or by the subject's monocytes. Diseases characterized by inflammatory responses which are mediated by T lymphocytes or monocytes are well known to those skilled in the art or examples of such diseases include, but are not limited to, rheumatoid arthritis.

In one embodiment of this invention the compound has the structure:

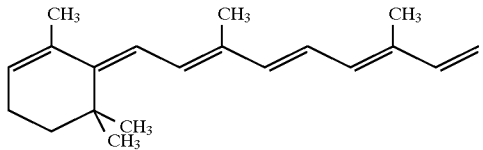

In another embodiment of this invention the compound has the structure:

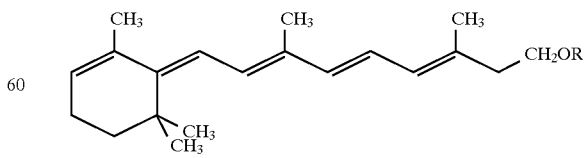

wherein R is H or a $C_1$–$C_{20}$ alkyl group.

In a further embodiment of this invention the compound has the structure:

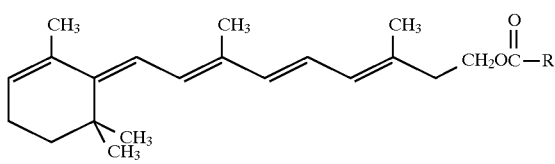

wherein R is H or a $C_1$–$C_{20}$ alkyl group.

In a further embodiment of this invention, the compound has the structure:

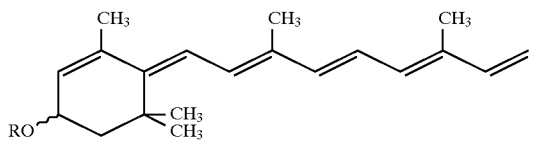

wherein R is H or a $C_1$–$C_5$ alkyl group.

In the preferred embodiment, the compound is administered in a composition which comprises the compound and a pharmaceutically acceptable carrier. As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptible triglyceride emulsion useful in intravenous and intraperetoneal administration of the compounds is the triglyceride emulsion commercially known as Intralipid®.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the preferred embodiment of the invention, the pharmaceutically acceptable carrier also comprises specific binding proteins, which may be, but are not limited to retinol binding protein (RBP), transthyretin (TTR), the complex formed by RBP and TTR, or albumin.

Compositions comprising such carriers are formulated by well known conventional methods. However, the composition comprising the compound or a pharmaceutically acceptable salt thereof in an amount effective to supress an inflammatory response is previously unknown.

In the practice of this method, the administration of the composition may be effected by any of the well known methods including, but not limited to, oral, intravenous, interperitoneal, intramuscular, subcutaneous or topical administration. Topical administration can be effected by any method commonly known to those skilled in the art and include, but are not limited to, incorporation of the pharmaceutical composition into creams, ointments or transdermal patches.

The present invention is further illustrated in the Experimental Details section which follows. The Experimental Details section is set forth to aid in an understanding of the invention but is not intended to, and should not be construed to, limit in any way the invention as set forth in the claims which follow thereafter.

Experimental Details

EXAMPLE 1

High Pressure Liquid chromatography of Retinoids

Cells [10×10⁶M cells in 10 ml of RPMI/7% fetal calf serum or Grace's insect medium/7% fetal calf serum] were incubated with 10 μCi [³H] retinol; specific activity, 49.3 Ci/mmol. After 4 hours (FIGS. 1A and 1B) or after 16 hours (FIG. 1C) retinoids were extracted from the washed cell pellet according to the procedure of McClean et al. (16). Retinoids were separated on an analytical $C_{18}$ reversed-phase column and detected with an on-line scintillation counter using the methodology described in Buck et al. (4). AR was the predominant metabolite in SF 21 (FIG. 1B) but was undetectable in SF-9 cells (FIG. 1A), a subclone of SF 21. Lymphoblastoid 5/2 also produced AR (FIG. 1C). The peak eluting at minute 29 is the all-trans anhydroretinol, whereas the companion peaks at minute 27 and 28 represent cis-isomers (14). All isomers yield spectra with characteristic vibronic fine structure similar to the spectrum of all-trans AR.

EXAMPLE 2

Inhibition of Human B Lymphoblastoid Tumor Cells

Anhydroretinol (AR) was produced from all-trans retinol by hydrochloric acid catalyzed dehydration as described (10), and the all-trans isomer was purified to homogeneity by reverse-phase high pressure liquid chromatography. Human B lymphoblastoid cells (e.g., cell line 5/2) were cultured in medium RPMI 1640 with 7% fetal calf serum. On the day of the assay, cells were washed and transferred to serum-free medium, RPMI 1640 supplemented with insulin, transferrin, linoleic acid, and bovine albumin (ITLB medium) as described (3). Test reagents at indicated concentrations were added to triplicate cultures of $5 \times 10^{13}$ cell/well in 96 well plates (final volume of 200 μl/well) and cell proliferation tested 1 day (FIGS. 2B, 2C, 2D) or 3 days later (FIG. 2A) by ³H thymidine incorporation into DNA. The agonists used were all-trans retinol (FIG. 2A), 14HRR (FIG. 2B) and fetal calf serum (FIG. 2C). Serum contains $1-2 \times 10^{-6}$M all-trans retinol. Three additional human lymphoblastoid cell lines, Hom 2, Jest and Ducaf were tested under the conditions specified for FIG. 2A (FIG. 2D).

EXAMPLE 3

Inhibition of Human T Cell Leukemia Cells

The T cell leukemia line Jurkat was transferred from normal, FCS-containing medium to serum-free medium ITLB. Cultures were then supplemented with $4 \times 10^{-6}$M retinol, or propagated without retinol (control). Cells were counted daily differentially in the presence of trypan blue, and the total number of cells generated in each culture plotted in FIG. 3A. It is evident that cells deprived of retinol decline in numbers as compared to cells with retinol. However, during the decline, the reintroduction of retinol allows rescue of the cells (see increase after day 6). These data indicate that Jurkat cells are retinol-dependent, although they do not die as rapidly as 5/2 cells when deprived of retinol.

EXAMPLE 4

Inhibition of Activation of Normal Resting T Cells

Murine thymocytes (2×10⁵/well in triplicates) were cultured in ITLB medium in 96-well plates coated with 10 μg/ml anti-CD3ᵉ mAB (12) as described (3). The retinoid agonists, retinol (FIG. 4A) or 14HRR (FIG. 4B), were added along with AR at different doses in checkerboard fashion. Cell proliferation was tested on day 3 by ³H thymidine incorporation into DNA. In FIG. 3C the time of addition of AR at different concentrations was varied from 0 hour to 54 hours after initiation of cultures with anti-CD3 plus $2\times10^{-6}$M retinol. The results of cell proliferation assays performed at 72 hours are shown. Culture supernatants of anti-CD3 plus retinol/AR-stimulated thymocytes were tested after 18 hours for their IL-2 content by the ability to stimulate the cell line CTLL (13). CTLL proliferation was measured by $^3$H thymidine incorporation into DNA (FIG. 4D). The standard deviation of triplicate measurements were <10%. The CTLL cell line was tested in the presence of recombinant IL-2 for responsiveness to retinol and AR over broad dose ranges and found independent of either retinoid (data not shown).

EXAMPLE 5

Inhibition of T Cell Activation by Retro-retinyl-methyl-ether

T lymphocytes from the mouse thymus were activated by monoclonal antibody 2c11 immobilized at the bottom of plastic multiwell culture plates as described by Garbe et al. (3). The culture medium, free of serum, was enriched with retinol at three different concentrations as shown in FIG. 4, to promote T cell activation. The retinoid, retro-retinyl-methyl-ether (See Table 2, compound III) was added at different serial dilutions covering a concentration range from $10^{-5}$M to approximately $10^{-9}$M. Cell proliferation was measured after three days of culture by tritium thymidine incorporation. The results in FIG. 4 indicate that retro-retinyl-methyl ether is capable of reversing the growth-promoting effect of retinol at an effective concentration range of from $10^{-5}$M to $10^{-8}$M.

EXAMPLE 6

Inhibition of Proliferation of Tumor Cells

Figure 6A:
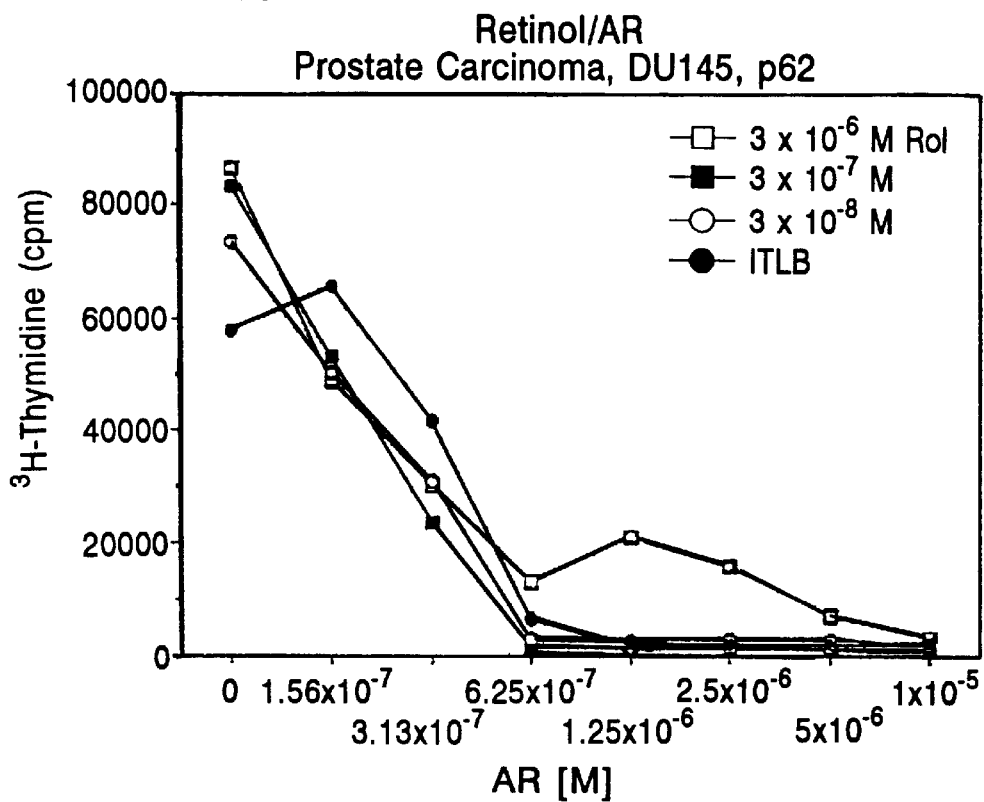
Figure 6B:
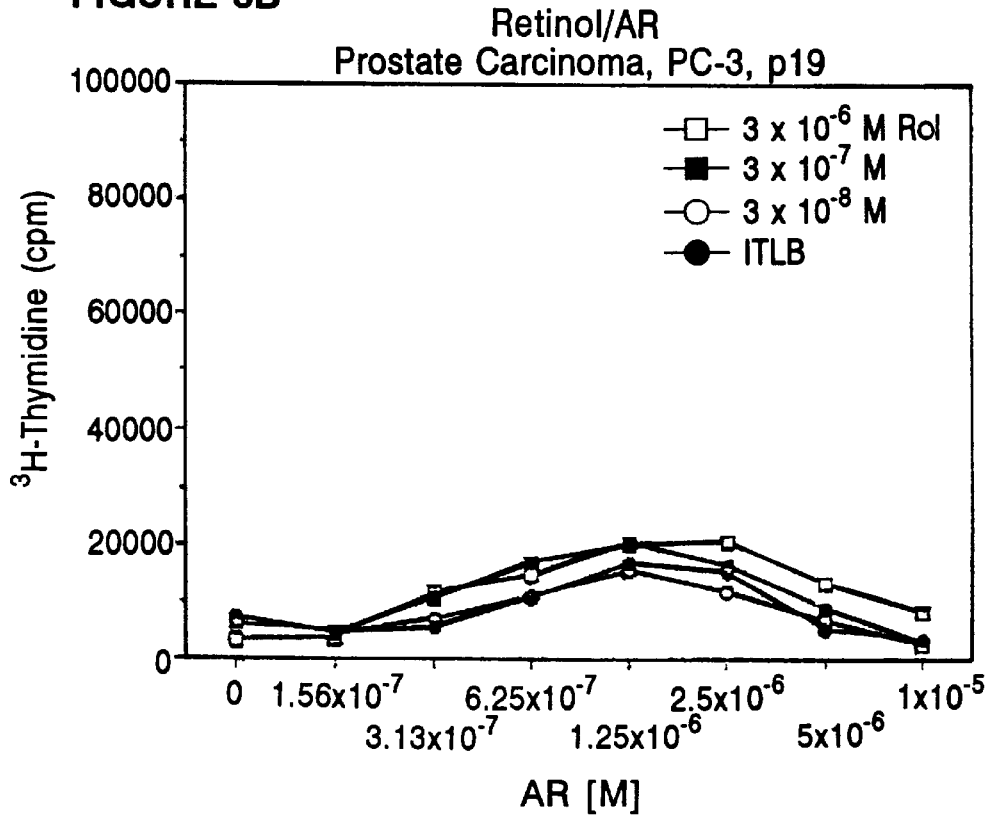

Cancer cell lines were treated with titrations of retinol vs. anhydroretinol (AR) concentrations and measured for 3H-thymidine incorporation as noted in Example 5. FIGS. 6A–6B show titrations for the inhibition by AR of prostate carcinoma cell lines DU145, PC-3 and LNCAP. The inhibition varies among the three cell lines, with DU145 having the highest sensitivity followed by PC-3. LNcAP appears to be insensitive to AR, which may be related to a longer doubling time for this cell line (note different ordinate scale for LNcAP). Table 4 shows additional cancer cell lines tested for their sensitivity to AR. The table demonstrates wide applicability of the methods of this invention to various tumor types.

EXAMPLE 7

Induction of Lymphocyte Cell Mortality

Figure 7:
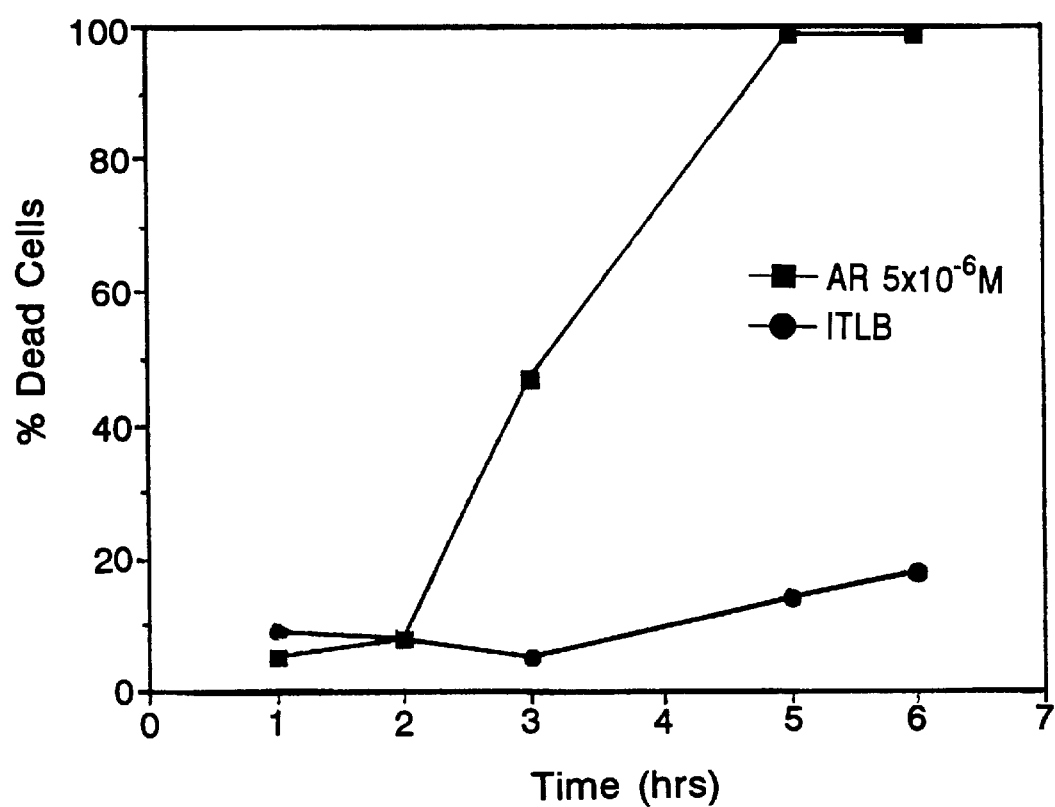
FIG. 7 Effect of Anhydroretinol on lymphocyte mortality in ERLD cells.

Murine T leukemia cells, ERLD, were treated with anydroretinol ($5\times10^{-6}$M) or defined serum-free medium, ITLB, and assayed for cell mortality by trypan blue uptake at hourly intervals. See FIG. 7.

Discussion

Figure 1D:
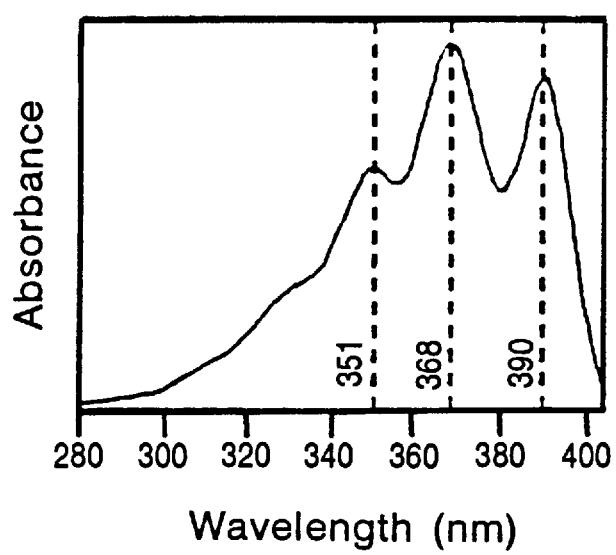

The compounds of this invention were synthesized according to known methods. Structures of representative compounds of the invention and the references discussing their preparation are listed in Tables II and III. Synthetic anhydroretinol (AR) was produced by acid catalyzed dehydration of all-trans retinol (10,11). AR is not metabolized by lymphocytes to retinol or to 14-hydroxy-retro-retinol (14-HRR) (unpublished data), nor does it support B cell proliferation (FIG. 2A). On the contrary, when AR was added to B cell cultures maintained in ten percent fetal bovine serum containing medium, strong growth inhibition was observed (FIG. 2C). Because of the structural relationship (FIG. 1), competitive antagonism by AR of retinol or 14-HHR was a likely possibility. Assays of human lymphoblastoid cell in serum-free medium supplemented with either retinol, i.e. the precursor of 14-HRR, (FIG. 2A) or 14-HRR itself (FIG. 2B) verified that AR was a competitive antagonist. The inhibitory dose ($ID_{50}$) of AR was dependent on the agonist concentration. For instance, AR at a concentration of $5\times10^{-6}$M displayed clear antagonism for $3.7\times10^{-6}$M retinol or $1.3\times10^{-6}$M 14-HHR, respectively (see FIGS. 2A and 2B), whereas progressively lower concentrations of agonist were neutralized by similarly reduced AR concentrations.

Because retinol, when applied in the absence of its natural extracellular carrier retinol binding protein, RBP, might create an unphysiological situation, we examined the effects of AR in B cell cultures supported with graded concentrations of fetal calf serum (FIG. 2C), or of RBP/retinol complex (data not shown). In both cases, AR was strongly inhibitory, displaying $ID_{50}$ values comparable to those seen in retinol-supplemented cultures. Several randomly selected human lymphoblastoid cell lines and a murine B cell lymphoma all proved sensitive to inhibition by AR, indicating a general dependence among B cells on retinol as an agonist and a corresponding susceptibility to AR as an antagonist (FIG. 2D).

Activation of resting thymocytes by T cell receptor-generated signals in serum-free medium was previously shown to be dependent on retinoid cofactors, retinol or 14-HRR (3). To test whether AR would interfere with the process as well, murine thymocytes were stimulated with immobilized anti-CD3 antibody and retinol or 14-HRR as cofactors, and various concentrations of AR. Inhibition of thymocyte activation was pronounced, depending on the relative concentrations of agonist, i.e. retinol or 14-HRR, and AR, as illustrated by the series of dose-response curves in FIGS. 4A and 4B. The interrelationship between agonist and antagonist was comparable to that observed in B lymphocytes. AR not only prevented the activation of thymocytes, but was also able to reduce the thymidine uptake of cycling thymocytes if given 2 days after activation (FIG. 4C).

While retinol is required for induction of T cell proliferation, other consequences of receptor mediated activation of resting T cells are independent of retinoid cofactors. We knew from previous unpublished work that interleukin-2 (IL-2) production and IL-2 receptor expression were unaffected by the presence or absence of retinol or 14-HRR. As expected, AR did not interfere with IL-2 release as shown in FIG. 4D. Therefore, the AR effect on proliferation is not due to a generalized toxicity. Because IL-2 measurements are predicated on the use of the IL-2-dependent cell line CTLL, it was important to demonstrate that retinoids carried over from the primary cultures would not positively or negatively affect CTLL proliferation. This was verified in control experiments with retinol, 14-HRR and AR, all of which proved completely inert vis-a-vis CTLL proliferation. This is compatible with previous unpublished observations that established Il-2 dependent $T_H$ cell clones and T cell hybridoma grow independently of retinol and 14-HRR.

A common feature in the physiology of retinoids is the use of intracellular and extracellular binding proteins, often specialized for particular retinoids, for protection against oxidative degradation and for transport. Retinol and 14-HRR bind to retinol-binding protein of plasma with similar affinities (Table 1). More significantly, retinol and AR bind to cellular retinol-binding protein (CRBP) with dissociation constants of 0.013 and 0.023 $\mu$M, respectively.

Therefore, competitive inhibition at the level of CRBP is a realistic possibility to explain the retinol-AR antagonism. For instance, if the CRBP/retinol complex were required for 14-HRR biosynthesis, disruption by the AR antagonist might interfere with this step. However, we found no change in the metabolic rate of 14-HRR synthesis from $^3$H labelled retinol in the presence of a hundredfold excess of AR (data not shown) and conclude from this experiment that CRBP is not involved in the biological retinol-AR antagonism. Moreover, the facts that 14-HRR does not bind to CRBP with appreciable affinity (Table 1) and that AR also reversibly inhibits cultures of lymphocytes when 14-HRR is provided as an agonist (FIGS. 2B and 4B) imply interference at a point downstream of, or in addition to, CRBP. By inference, a separate 14-HRR binding protein/receptor, as yet to be defined, may exist.

Our finding of antagonism between the compounds of this invention and retinol or 14-HRR contributes to the understanding of the mechanism of action of retinol. These results are compatible with the previously presented view that retinol is engaged in the regulation of cell physiology by a second messenger pathway with 14-HRR as the likely mediator. Furthermore, the marked inhibition by the compounds of T cell activation and proliferation of B lymphoblastoid cells is the basis for this patent application on the immunosuppressive and/or antiproliferative properties of anhydroretinol.

TABLE 1

Dissociation constants of retinoids bound to extra- or intracellular binding proteins.

| retinoid | dissociation constant ($\mu$M) | | |
|---|---|---|---|
| | RBP | CRBP I | CRABP I |
| retinol | 0.15* | 0.013 | no binding |
| 14-HRR | 0.12 | no binding | no binding |
| AR | 0.020 | 0.023 | no binding |

*Data as reported by Cogan et al. (14).
no binding = no significant binding could be detected Dissociation constants of retinoids to serum retinol binding protein (RBP), cellular retinol binding protein (CRPB I) and cellular retinoic acid binding protein (CRABP I) were measured by fluorometric titration. Apo-protein (1–3 $\mu$M) was titrated with the appropriate all-trans-retinoid dissolved in ethanol and the titration was followed by measuring the increase in the fluorescence of the retinoids upon binding. Reaction mixtures included 150 mM NaCl, 0.1 mM DTT, and 25 mM HEPES; pH's were 7.0 and 7.4, respectively. Retinoid fluorescence was measured at the excitation and emission maxima for the different retinoids: i.e. excitation— 330, 350, and 368 nm; emission—480, 515, 570 nm for retinol, 14-HRR and AR respectively. Data analyses were performed as described by Cogan et al. (14). Human RBP was purified from human serum by means of a transthyretin column (15). Human CRBP I and CRABP I were gifts from Dr. W. S. Blaner (Columbia University, New York, N.Y.) and Dr. J. Napoli (SUNY, Buffalo, N.Y.), respectively.

TABLE 2

The following compounds having antagonist properties have been synthesized according to known methods.

| Compound | Structure |
|---|---|
| I. Anhydroretinol (11,17) | 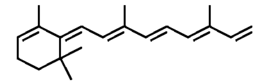 |
| II. 4,14-Retro-retinol (18,19) | CH$_2$OH |
| III. 4,14-Retro-retinyl methyl ether (20) | CH$_2$OMe |
| IV. 4,14-Retro-retinyl acetate (21) | CH$_2$—OC(O)—CH$_3$ |
| V. 3 Methoxy-anhydroretinol (22) | CH$_3$O''' |

TABLE 3

The following related compounds can also be synthesized according to known methods.

| Compound | Structure |
|---|---|
| VI. 3-Ethoxy-anhydroretinol (22) | CH$_3$CH$_2$O''' |
| VII. 3-Hydroxy-anhydroretinol (23) | HO''' |
| VIII. 3-Acetoxy-anhydroretinol (23, 24) | CH$_3$—C(O)—O''' |
| IX. True anhydro-vitamin A$_2$ (22) | 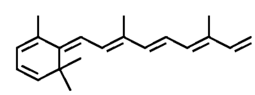 |
| X. Retro-3-dehydroretinol (25) | CH$_2$OH |
| XI. Retro-3-dehydroretinyl esters (25) | CH$_2$OCR (O); R = CH$_3$, R = PALMITYL |
| XII. 4,14-Retroretinoic acid (26) | COOH |

TABLE 3-continued

The following related compounds can also be synthesized according to known methods.

| Compound | | Structure |
|---|---|---|
| XIII. | Ethyl 4,14-retro-retinoate (26) | 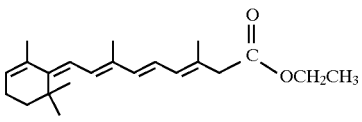 |

TABLE 4

Tumor Cell Sensitivity to Anhydroretinol

| Cell line | Sensitivity |
|---|---|
| Prostate Carcinoma | |
| PC-3 | + |
| DU145 | ++ |
| LNcAP | − |
| Lung Carcinoma | |
| SK-LC 13 | + |
| SK-LC 17 | + |
| Pancreatic Carcinoma | |
| ASPC-1 | + |
| Neuroblastoma | |
| LA1-5s | ++ |
| LA1-5n | + |
| SK-N-MC | + |
| Colon Carcinoma | |
| SK-CO 1 | − |
| SK-CO 10 | + |
| SW-620 | + |
| Renal Carcinoma | |
| SK-RC 7 | ++ |
| CV-1 | + |
| Breast Carcinoma | |
| MCF-7 | + |
| 734B | ++ |
| SK-BR 3 | + |
| SK-BR 5 | + |
| Melanoma | |
| SK-MEL 23 | + |
| SK-MEL 28 | + |
| SK-MEL 31 | + |

REFERENCES

1. Buck, J., et al., *J. Exp. Med.,* 171:1613–1624 (1990).
2. Buck, J., et al., *J. Cell Biol.,* 115:851–859 (1991).
3. Garbe, A., Buck, J., Hammerling, U., *J. Exp. Med.,* 176:109–117 (1992).
4. Buck, J., et al., *Science,* 254:1654–1656 (1991).
5. The Retinoids (eds Sporn, M. B., Roberts, A. B. & Goodman, D. S.) (Academic, Orlando, 1984).
6. Wald, G., *Science,* 162:230–2 (1968).
7. Roberts, A. B., & Sporn, M. B., in *The Retinoids*, Vol. 2, (eds Sporn, M. B., Roberts, A. B., & Goodman, D. S.) pp. 209–286 (Academic, Orlando, 1984).
8. Evans, R. M., *Science,* 240:889–895 (1988).
9. Green, S., and Chambon, P., *Trends in Genet.,* 4:309–314 (1988).
10. Embree, N. D., *J. Biol. Chem.,* 128:187–198 (1939).
11. Edisbury, J. R., et al., *Biochem. J.,* 26:1164–1173 (1932).
12. Leo, O., et al., *Proc. Natl. Acad. Sci. USA,* 84:1374–1378 (1987).
13. Gillis, S., and Smith, K. A., *Nature,* 268:154–156 (1977).
14. Cogan, U., et al., *Eur. J. Biochem.,* 65:71–78 (1976).
15. Fex, G., and Lindgren, R., *Biochim. Biophys. Acta,* 493:410–416 (1977).
16. McLean, S. W., et al., *Clin. Chem.,* 28:693 (1982).
17. Shantz, E. M., et al., *J. Am. Chem. Soc.,* 65:901 (1943).
18. Gobwein, L., University of Wurzburg, (Diplomarbeit 1976).
19. Schreckenbach, T., et al., *Photochem. Photobio.,* 28:205 (1978).
20. Oroshnik, W. et al., *J. Am. Chem. Soc.,* 74:295 (1952).
21. Beutel, R. H., et al., *J. Am. Chem. Soc.,* 77:5166 (1955).
22. Henbest, H. B., et al., *J. Chem. Soc.,* 2763 (1955).
23. Bania, A. G., et al., *Biochem. J.,* 177:791 (1979).
24. Burua, R. K., & Nayar, P. G., *Biochem. J.,* 101:302 (1966).
25. Krishna, A., et al., *Biochem. J.,* 109:293 (1968).
26. Huisman, et al., *Rec. trav. chim.,* 75:977 (1956).

What is claimed is:

1. A method of inhibiting the growth of cells, wherein the cells are growth-dependent on retinol or 14-Hydroxy-retroretinol, which comprises contacting the cells with an effective growth inhibiting amount of a compound having the structure:

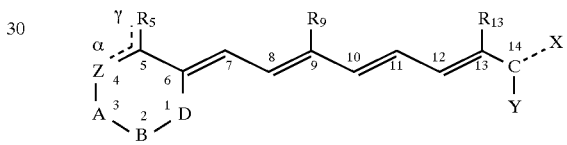

wherein Z represents:

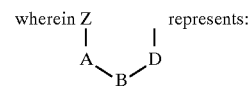

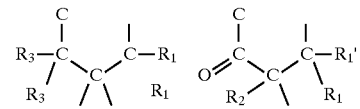

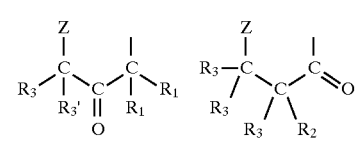

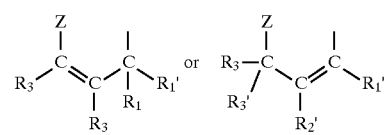

$R_1$, $R_1'$, $R_2$, $R_2'$, $R_3$ and $R_3'$ are independently H, halide, $C_1$–$C_5$ alkyl or alkyl halide,

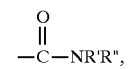

wherein each of R' and R" are independently H or a $C_1$–$C_{20}$ alkyl group; or —O—R, wherein R is H, a $C_1$–$C_5$ alkyl group or has the structure:

wherein R' is a $C_1$–$C_{20}$ alkyl group;
R$_9$ and R$_{13}$ are H, a halide, or a $C_1$–$C_5$ alkyl or alkyl halide group;
X is —CH$_2$;

wherein R is H or $C_1$–$C_{20}$ alkyl; or CH$_2$OR, wherein R is H, a $C_1$–$C_{20}$ alkyl or has the structure:

wherein R' is H, a $C_1$–$C_{20}$ alkyl or alkyl halide, or is —NR'R" wherein each of R' and R" are independently H, or a $C_1$–$C_{20}$ alkyl group; the dashed line between $C_{14}$ and X represents a single bond when
X is —CH$_2$OR or

and a double bond when X is —CH$_2$;
Y is H;
the double bonds between $C_6$ and $C_7$, $C_8$ and $C_9$, $C_{10}$ and $C_{11}$, and $C_{12}$ and $C_{13}$ can have Z or E configuration; the absolute configuration at $C_{14}$ is either R or S; and
wherein one of the dashed lines at $C_5$ represents a double bond which can be either α or γ and the other represents a single bond;
wherein when the double bond at $C_5$ is Y R$_5$ is $C_1$–$C_5$ alkylidene or haloalkylidene and Z is C=O or CR$_4$R$_4$ wherein R$_4$ and R$_4$, are independently the same as R$_1$ and R$_1$, through R$_3$ and R$_3$, defined above; wherein when the double bond at $C_5$ is α R$_5$ is $C_1$–$C_5$ alkyl or alkylhalide and Z is CR$_{4'}$ wherein R$_{4'}$ is the same as defined above;
with the priviso that if X is —CH$_2$, then Y is not H to thereby inhibit the growth of the cells.

2. The method of claim 1, wherein the compound has the structure:

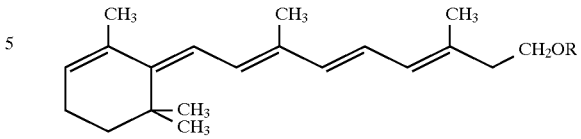

wherein R is H or a $C_1$–$C_{20}$ alkyl group.

3. The method of claim 1, wherein the compound has the structure:

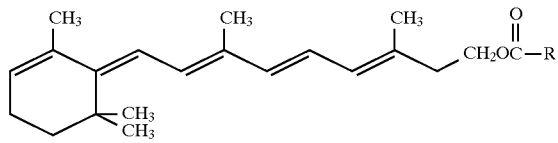

wherein R is H or a $C_1$–$C_{20}$ alkyl group.

4. The method of claim 1, wherein the compound has the structure:

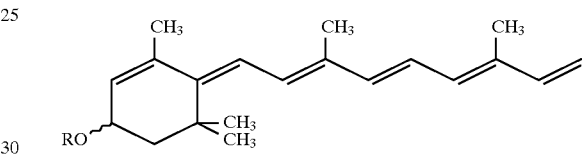

wherein R is H or a $C_1$–$C_5$ alkyl group.

5. The method of claim 1, wherein the cells growth-dependent on retinol or 14-Hydroxy-retroretinol are tumor cells, activated T cells, transformed B cells or myeloid cells.

6. The method of claim 1, wherein the cells growth-dependent on retinol or 14-Hydroxy-retroretinol are tumor cells.

7. The method of claim 6, wherein the tumor cells are B-cell lymphomas or leukemias.

8. The method of claim 6, wherein the tumor cells are T-cell lymphomas or leukemias.

9. The method of claim 6, wherein the tumor cells are myeloid leukemia cells.

* * * * *